United States Patent
Tang et al.

(10) Patent No.: US 7,801,394 B2
(45) Date of Patent: Sep. 21, 2010

(54) SENSITIVE EMISSION LIGHT GATHERING AND DETECTION SYSTEM

(75) Inventors: Cha-Mei Tang, Potomac, MD (US); Platte T. Amstutz, III, Vienna, VA (US)

(73) Assignee: Creatv Microtech, Inc., Potomac, MD (US)

( * ) Notice: Subject to any disclaimer, the term of this patent is extended or adjusted under 35 U.S.C. 154(b) by 824 days.

(21) Appl. No.: 11/541,785

(22) Filed: Oct. 3, 2006

(65) Prior Publication Data

US 2010/0208256 A1 Aug. 19, 2010

Related U.S. Application Data

(60) Provisional application No. 60/722,428, filed on Oct. 3, 2005.

(51) Int. Cl.
*G02B 6/32* (2006.01)
*G02B 6/42* (2006.01)
*G02B 6/00* (2006.01)

(52) U.S. Cl. .............................. 385/12; 385/31; 385/33; 385/36; 385/39; 385/49

(58) Field of Classification Search ................... 385/12, 385/31, 33, 36, 39, 49
See application file for complete search history.

(56) References Cited

U.S. PATENT DOCUMENTS 4,867,559 A * 9/1989 Bach ........................... 356/73
6,188,813 B1 * 2/2001 Dourdeville et al. .......... 385/12
6,332,049 B1 12/2001 Dasgupta
6,813,427 B1 11/2004 Kaltenbacher et al.

FOREIGN PATENT DOCUMENTS

CN 2166469 Y 2/2001

* cited by examiner

*Primary Examiner*—Ryan Lepisto
(74) *Attorney, Agent, or Firm*—Roylance, Abrams, Berdo & Goodman, L.L.P.

(57) ABSTRACT

A luminometer is provided comprising a waveguide sample holder and one or more detectors. The waveguide sample holder may include a hollow region to hold the sample. The waveguide sample holder can be made of material that guides emission light to a bottom end of the waveguide sample holder. One or more detectors may be provided which detect the emission light coming out of the bottom of the waveguide sample holder. A fluorometer/photometer is also provided that comprises a waveguide sample holder, one or more excitation light sources, and one or more optical detectors. The waveguide sample holder has a hollow region to hold the sample. The excitation light is introduced at an angle or perpendicular to one surface of the waveguide sample holder. The waveguide sample holder is made of material that can guide emission light to the bottom end of the waveguide sample holder. There are one or more detectors that detect the emission light coming out of the bottom of the waveguide sample holder.

31 Claims, 24 Drawing Sheets

(a)

(b)

SENSITIVE EMISSION LIGHT GATHERING AND DETECTION SYSTEM

This application claims benefit under 35 U.S.C. §119 from U.S. Provisional Application No. 60/722,428, filed on Oct. 3, 2005, the entire content of which is incorporated herein by reference.

FIELD OF THE INVENTION

The invention relates to a sensitive luminescence detection system including at the minimum a waveguide sample holder that can hold the sample. The invention also relates to a system that includes an excitation light source and a sensitive detection system to detect the change of both the excitation and emission signals from samples in a waveguide sample holder. The waveguide sample holder is efficient in gathering and guiding the emission light to the detector. The waveguide sample holder design, the arrangement of the excitation light illumination, and optical filters may be configured to facilitate detection of very low concentrations of samples and emission reagents and for ease of use.

DESCRIPTION OF RELATED ART

As used herein, the term "Integrating Waveguide Sensor" technologies refer to the detection of excitation and emission signals on the surface of a waveguide or in solution inside a waveguide sample holder.

The solid phase implementation of the Integrating Waveguide Biosensor is based on detection using emission reagents on the surface of a waveguide. A light source appropriate to the emission reagent illuminates the optical waveguide at a 90 degree angle. The emitted signal is efficiently gathered by the waveguide and exits from the end of the waveguide. The emission signal is sent to the detector via a set of lenses and filters. This technique is described in Mark J. Feldstein, Brian D. MacCraith and Frances S. Ligler, "Integrating Multi-Waveguide Sensor," U.S. Pat. No. 6,137,117 issued on Oct. 24, 2000, and in Frances S. Ligler, Marc Breimer, Joel P. Golden, Delana A. Nivens, James P. Dodson, Tiffanee M. Green, Daniel P. Haders, and Omowunmi A. Sadik, "Integrating Waveguide Biosensor," Anal. Chem. 2002, 74, 713-719, and the entire disclosures of both of these documents is incorporated herein by reference.

SUMMARY OF THE INVENTION

An object of the present invention is the liquid phase implementation of the Integrating Waveguide Sensor where the emission reagents are in solution inside a container that can hold solution and the solution and the container together acts like a waveguide. A light source appropriate to the emission reagent illuminates the waveguide containing solution from a direction perpendicular to or at an angle to the surface of the waveguide sample holder. The emitted signal is efficiently gathered by the waveguide, along with the excitation light, and exits from the end of the waveguide. The excitation and emission signals are sent to the detector via a set of lenses and filters.

As used herein, the term "sample" is intended to mean predominantly a liquid and the liquid might also contain a variety of other materials, such as small solid particles, chemicals, molecules, proteins, DNA, emission reagents, micro-organisms, cells, and etc.

As used herein, the term "Optical Elements" includes elements comprising any one, or a combination, of lens(es), filter(s), optical waveguides (such as optical fibers, but excluding the waveguide sample holder), and gratings. The optical elements are used (1) to increase the signal (the emission light) which is increased by improved collection of emission light and improved guiding of the light to the detector using, for example, lens(es) and optical waveguides (such as optical fibers) and (2) to reduce noise, background and/or other undesirable sources of fluorescence by eliminating light from undesirable wavelengths using filter(s), gratings, etc.

As used herein, the term "waveguide sample holder" refers to a container that can hold a sample and the combination of the sample and the container act as a waveguide to guide emission light generated in the sample to the detector.

As used herein, the terms "Emission light" and/or "Emission Signal," refer to the light produced by luminescence, fluorescence, phosphorescence and/or other emission reagents include colloidal gold, colloidal silver, other colloidal metals and non-metals, plasmon resonant particles, quantum dots, other fluorescent nanoparticles, grating particles, photonic crystal reagents, and the like.

As used herein, the term "luminescence" refers to the production of electromagnetic radiation by a chemical or biochemical material that is used as or produced by an emission reagent. "Chemiluminescent" refers to the production of light when the excitation energy derived from a chemical reaction. "Bioluminescent" refers to a subset of chemiluminescence, where the light is produced by biological or biochemical reaction. A specific example of bioluminescence is the production of light by a firefly where the substrate Luciferin combines with the enzyme Luciferase and reactants ATP (adenosine triphosphate) and oxygen. "Electrochemiluminescence (ECL)" is a form of luminescence in which the light emitting chemiluminescent reaction is preceded by an electrochemical reaction.

As used herein, the term "fluorescence" refers to light emission following absorption of energy from an external source of light. Fluorescent emission can be from chemical or biochemical reagents. The wavelength that is emitted is longer than the wavelength that is absorbed. Specific examples of fluorescent materials include organic dyes, such as Cy-3 and Cy-5, AlexaFluor, green fluorescent protein (GFP), silicon nanoparticles, quantum dots, and a diverse collection of other materials well known in the art.

As used herein, the term "phosphorescence" refers to a phenomenon similar to fluorescence, except that the excited product is relatively more stable. Accordingly, the time until energy is released is longer compared to fluorescence, resulting in a glow after the excitation light has been removed. Phosphorescent emission also can be from a chemical or biochemical reagent.

As used herein, the term "emission reagent" refers to luminescent, fluorescent, or phosphorescent materials. Other emission reagents include colloidal gold, colloidal silver, other colloidal metals and non-metals, quantum dots, other fluorescent nanoparticles, plasmon resonant particles, grating particles, photonic crystals reagents and the like.

As used herein, the term "detector" refers to a device that can convert emission light produced by the sample or emission reagent to an electronic signal or image. Examples of detectors are photodiodes, one-dimensional charge-coupled device (CCD) arrays, two-dimensional CCD arrays, photomultiplier tubes (PMT), position sensitive PMTs, Complementary Metal. Oxide Silicon (CMOS) image arrays, spectrometers, etc. The detector can be chosen to have maximum sensitivity in the frequency region of emission light and can be provided with a filter blocking the excitation light source. One or more detectors can be used.

The emission signal produced by the emission reagent can be detected as total energy or as energy as a function of wavelength.

The emission signal produced by the emission reagent can be detected as instantaneous energy, time averaged, or time integrated energy. For emission reagents such as quantum dots, which can remain photo stable after exposure to long periods of excitation light sources as compared to organic dyes, integration of the signal over a longer period of time than organic dyes becomes possible and can be used to improve the sensitivity of detection.

As used herein, the term "excitation light source" refers to the radiation illumination member, comprised of light source(s) and optics. For some applications, such as colloidal gold and silver, the excitation light source can be a broad-spectrum source, while in other applications the excitation light source can be a narrow spectrum source. Some samples can be better illuminated using multiple light sources. In some multiple-analyte applications, for example, with more than one fluorescent emission reagent in the same sample, some emission reagents can require one or more narrow band excitation light sources, while other emission reagents, such as quantum dots, may be illuminated by a single narrow band or broadband excitation light source for all emission wavelengths. Lenses, filters, and other optical devices may be employed to achieve the desired or optimum illumination.

Excitation light source in the exemplary embodiments of the present invention can use any light source using any of various methods known in the art. Exemplary sources include lasers, light emitting diodes (LEDs), and other narrow and broadband light sources.

Briefly, light from a laser has the property of coherence and potentially high power, narrow wavelength band, and a beam that can be turned into a wide collimated beam, a cone beam, or a fan beam with lenses. Coherence and high power provide greater power density. Narrow band is desirable for organic dye emission reagents. Any kind of laser can be used in the apparatuses and methods of the exemplary embodiments of the invention. Diode lasers are commonly available, compact and relative low cost.

LEDs produce light that is not coherent and of broader bandwidth than lasers. LEDs are relatively inexpensive and compact. Therefore LEDs are well suited to some applications. Alternatively, an addressable multiple-element array of optical sources, such as LEDs, can be used to sequentially probe various fluorescent materials in the sample. This multiple element array of optical sources provides a particularly low cost technique, having the advantage of no moving parts, and providing more flexibility than stepped or oscillated excitation light, because LEDs or groups of LEDs would be addressable in any temporal or spatial sequence.

Broadband incoherent light sources including, for example, incandescent lamps, fluorescent lamps, xenon lamps, mercury lamps and arc lamps, are useful in the apparatuses of the exemplary embodiments of the invention. For example, broadband ultraviolet (UV) sources can be useful for illuminating quantum dots.

A wide variety of excitation light source configurations are possible for use in the radiation illumination member. The selection among alternatives will depend, in part, on the emission reagent and the sample.

In the exemplary embodiments of the invention, the temporal mode of radiation illumination and radiation detection can include, for example, a variety of methods and variations. Specific examples of such modes include instantaneous signal, time averaged instantaneous signal, time integrated partial signal, time integrated continuous whole signal, frequency modulated signals, or other variations or combinations thereof. The temporal mode of illumination and detection is related to the method of spatial illumination of the excitation light, the fluorescent emission reagent, the waveguide geometry, the number of analytes to be detected, the concentration level of the analyte, and the desired sensitivity of the detection.

Excitation light source can impinge on the emission reagent of the sample during the entire period of detection of each analyte. The excitation light source can be modulated or "chopped" to eliminate interference from ambient light. Demodulation of the resulting emitted signal, such as with a lock-in amplifier, can then reduce background interference. Such modulation may not be required, if ambient light is eliminated by optical isolation or shielding.

One method of illumination is for the excitation light source to emanate from a wide or diffused area, and to illuminate the entire sample from one or more directions. Advantages of this unfocused or diffused illumination method includes: (1) illuminating substantially the entire sample, (2) minimizing alignment procedures, since the illumination areas may be larger than the sample size.

One or more excitation light sources can be used sequentially or simultaneously to provide different illumination wavelengths and/or to provide different spatial and temporal coverage. The angle of incidence of the excitation light can be perpendicular to the incident surface of the waveguide sample holder, perpendicular to the length of the waveguide sample holder, or at one or more angles in relation to the surface of the waveguide sample holder. The optimal angle of illumination can be selected so as to reduce the background noise resulting from excitation light or to enhance any other desirable characteristics of the device. The excitation light can be collimated, non-collimated, point source, from multiple point sources, diffused source or broad area unfocused source. The angle of illumination need not be limited to excitation perpendicular to the surface of the waveguide sample holder.

An optimal angle of illumination is dependent on the size and shape of the waveguide sample holder and the desired detection limit. A long waveguide sample holder can reduce collected excitation light at the detector, because each time the excitation light reflects on a boundary of the waveguide sample holder, part of the excitation light is lost due to transmission out of the waveguide. The reflection loss is largest at the angle perpendicular to the surface of the waveguide sample holder.

One aspect of the exemplary embodiments of the invention is to provide a sensitive luminescence detection system comprising an instrument and a waveguide sample holder to hold the sample. The waveguide sample holder is efficient in gathering the luminescent emission light and guiding the light to the detector.

Another aspect of the invention is a system that includes an excitation light source and a sensitive detection system to detect the change of both the excitation and emission signals from samples in a waveguide sample holder. As stated above, the waveguide sample holder is efficient in gathering the emission light and guiding it to the detector. The waveguide sample holder design, the arrangement of the excitation light illumination, and optical filters may be configured to facilitate detection of very low concentrations of emission reagents and for ease of use.

To achieve the foregoing aspects of the exemplary embodiments for luminescence applications, a luminometer is provided comprising a waveguide sample holder and one or more detectors. The waveguide sample holder may include a hollow region to hold the sample. The waveguide sample holder can be made of material that guides emission light to the closed end of the waveguide sample holder. The instrument can include a device to introduce the sample and reagents into the waveguide sample holder. One or more detectors may be provided that detect the emission light coming out of the closed end of the waveguide sample holder. Examples are illustrated in FIGS. 1-8 and 23.

Also, to achieve the foregoing objects of the exemplary embodiments for fluorescence and absorbance applications, a fluorometer or photometer is provided that comprises a waveguide sample holder, one or more excitation light sources and one or more optical detectors. The waveguide sample holder has a hollow region to hold the sample. The excitation light is introduced at an angle or perpendicular to one surface of the waveguide sample holder. The waveguide sample holder is made of material that can guide emission light to the closed end of the waveguide sample holder. There are one or more detectors that detect the emission light coming out of the closed end of the waveguide sample holder, shown in FIGS. 9-19 and 22-23.

DETAILED DESCRIPTION OF EXEMPLARY EMBODIMENTS

An exemplary embodiment of a luminescence applications based on the liquid phase implementation of the Integrating Waveguide Sensor is shown in FIGS. 1*a,b*. A luminometer comprises a waveguide sample holder and one or more detectors. The waveguide sample holder has a hollow region to hold the sample. Sample and reagents can be manually place or pumped by instrument into the sample and reagent placement chamber. The waveguide sample holder can be made of material that guides emission light to the bottom end of the waveguide sample holder. One or more detectors may be provided which detect the emission light coming out of the bottom of the waveguide sample holder.

A variety of suitable constructions and arrangements may be used for the luminometer and the components of the luminometer.

For example, as shown in FIG. 1a, the outer shape of the waveguide sample holder may have an axially symmetrical conical shape. Also in FIG. 1a, a curved surface at the end is provided to focus or collimate the emission light exiting the waveguide sample holder and to contain the sample.

In FIG. 1b, the cross-sectional shapes of the outer surface of the waveguide sample holder and of the sample area may be round.

Figure 1:
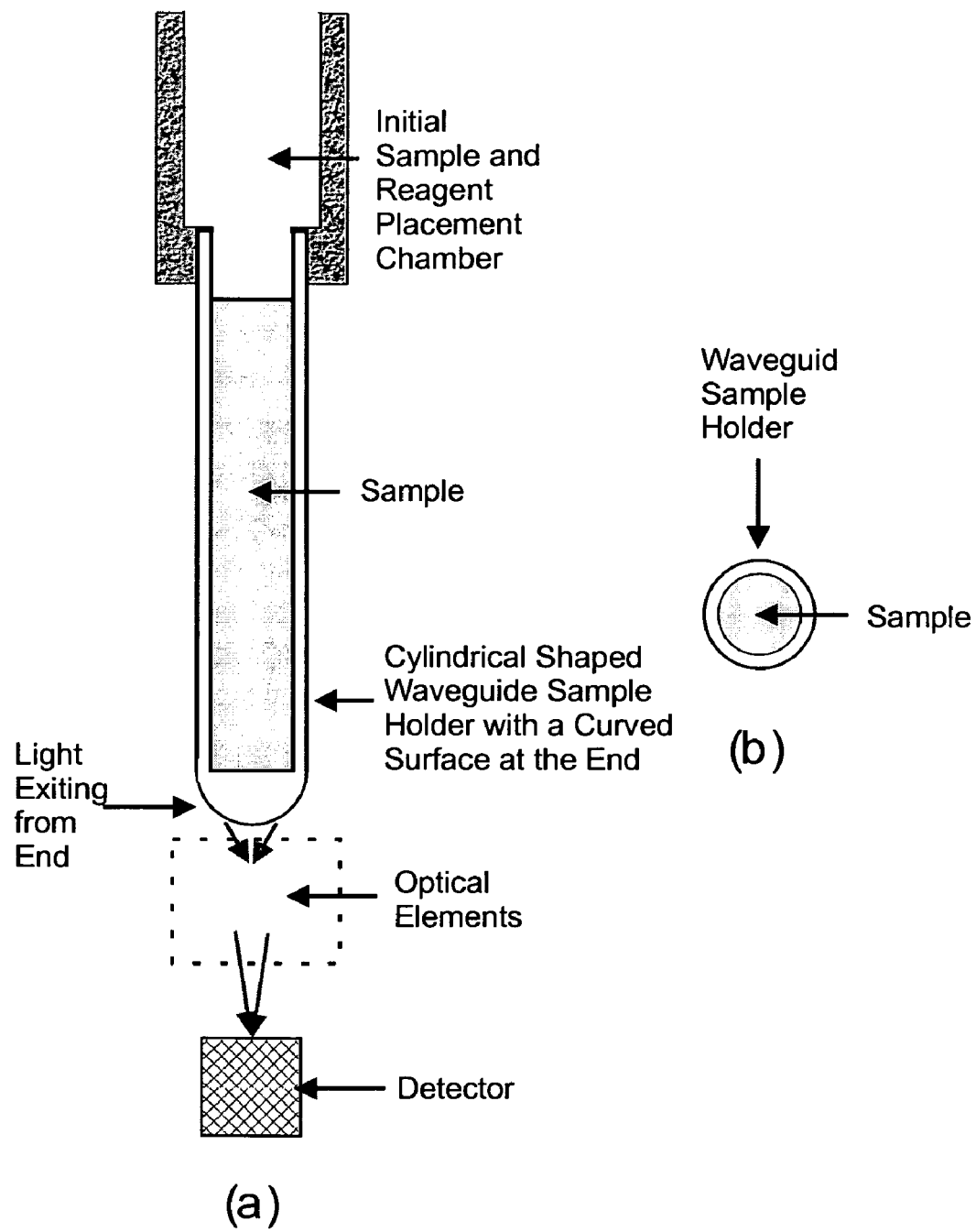
FIG. 1. (*a*) Schematic side view of luminescent detection system, where the waveguide sample holder has a round same cross sectional shape along its length and a curved surface at one end to focus optical signal. Additional optical elements are needed to focus the optical signal to the detector. (*b*) Cross sectional view of the waveguide sample holder.

There may be a sample placement chamber at the open end of the waveguide sample holder as shown in FIG. 1a. There can be a set of optical elements to focus, guide or filter the emission light to the detector, as shown in FIG. 1. The detector can be one of the following: spectrometer, PMT, CCD, CMOS imaging arrays or photodiode, or any other optical detector.

Figure 2:
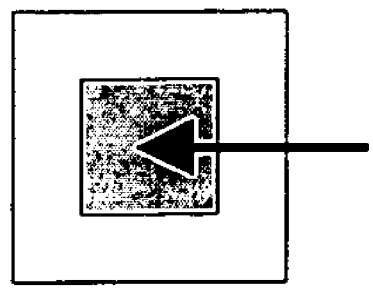
FIG. 2. Cross sectional views of the waveguide sample holder alternative cross sectional shapes: (*a*) Square inside and outside shapes and (*b*) square outside and round inside.
Figure 2:
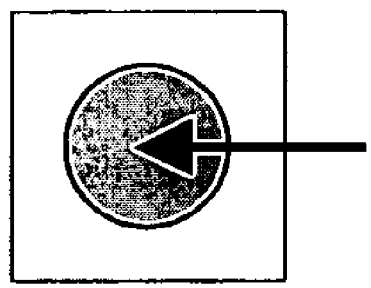

The cross-sectional shapes of the outer surface of the waveguide sample holder and of the sample area can be both square, as shown in FIG. 2a. The cross-sectional shape of the outer surface of the waveguide sample holder and the sample area are not limited to these geometries and other suitable shapes and arrangements may be used. Any suitable shape that provides a good guide of light to the exit end of the waveguide sample holder can be used. The cross-sectional shapes of the outer surface of the waveguide sample holder can have one shape, for example, square, and the cross-sectional shape of the sample area can have a different shape, round for example, as shown in FIG. 2b.

Figure 3:
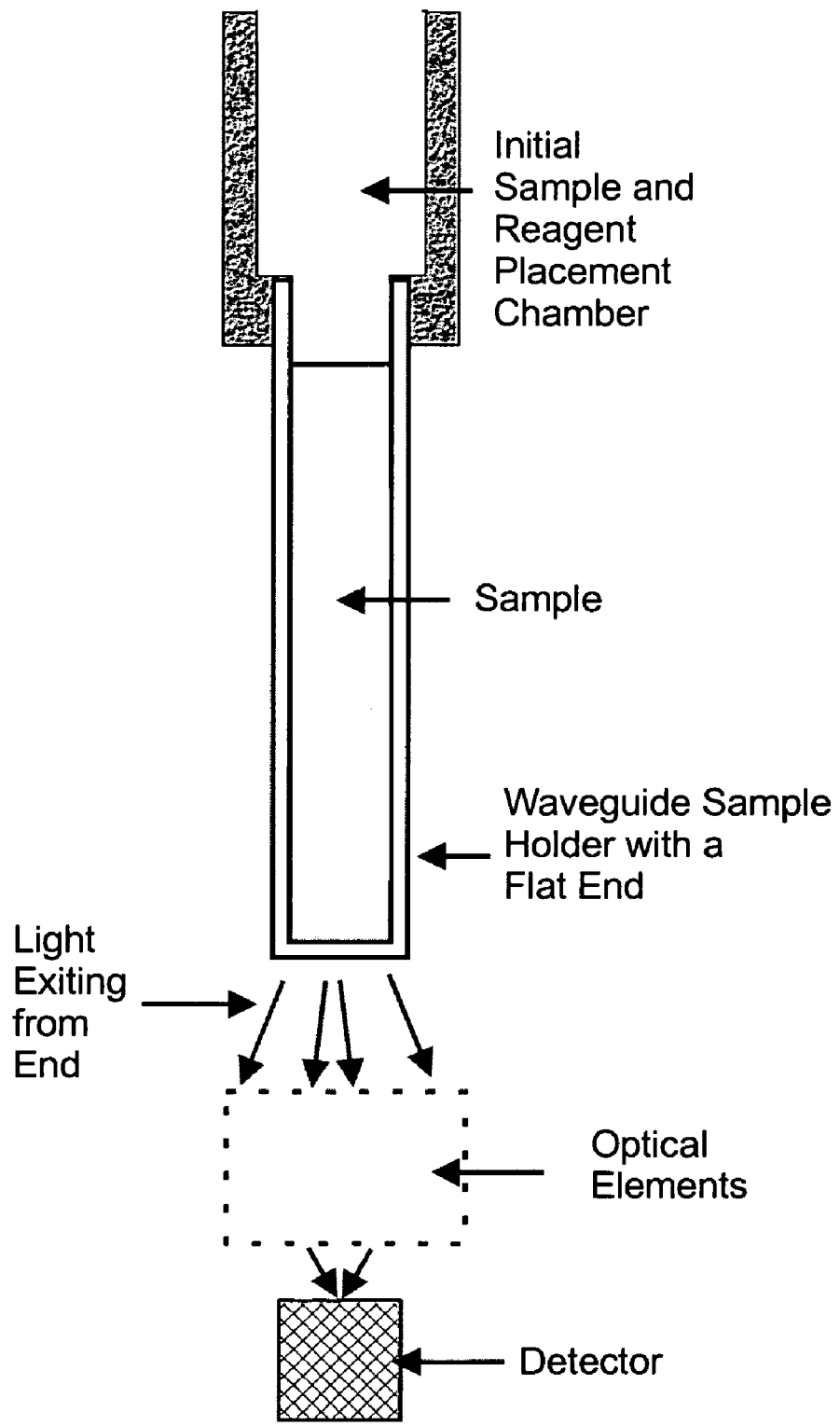
FIG. 3. Variation of waveguide sample holder with no lens at the closed end.

A waveguide sample holder with a flat surface at the end is shown in FIG. 3.

Figure 4:
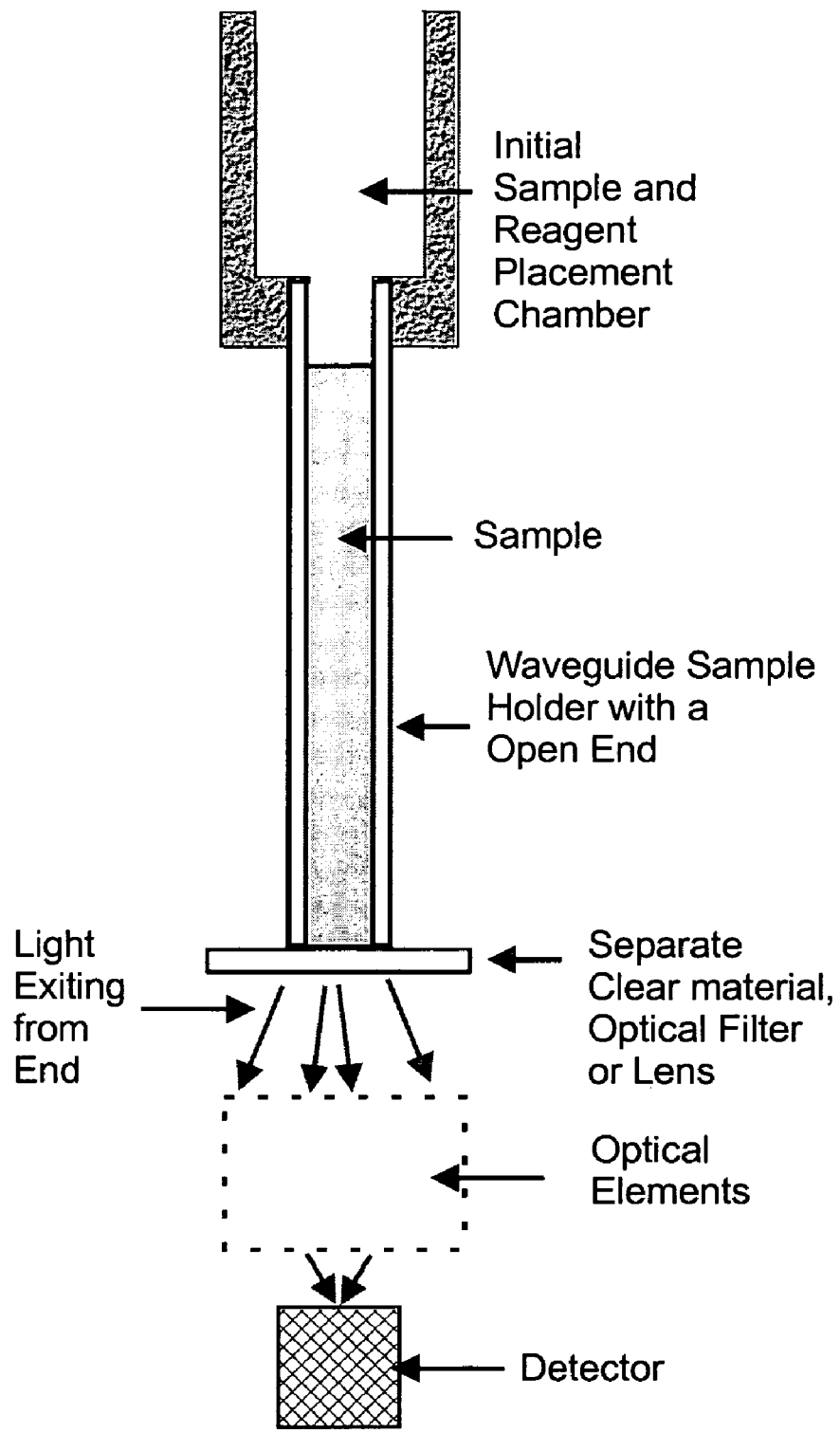
FIG. 4. Schematic side view of luminescent detection system, where the waveguide sample holder is open on both ends, and it can be placed in close proximity to a flat clear material (as drawn in figure), an optical filter (not drawn in figure) and/or a lens (not drawn in figure).

The waveguide sample holder is open on both ends, and it can be placed in close proximity to a flat clear material, an optical filter, or a lens, as shown in FIG. 4.

Figure 5:
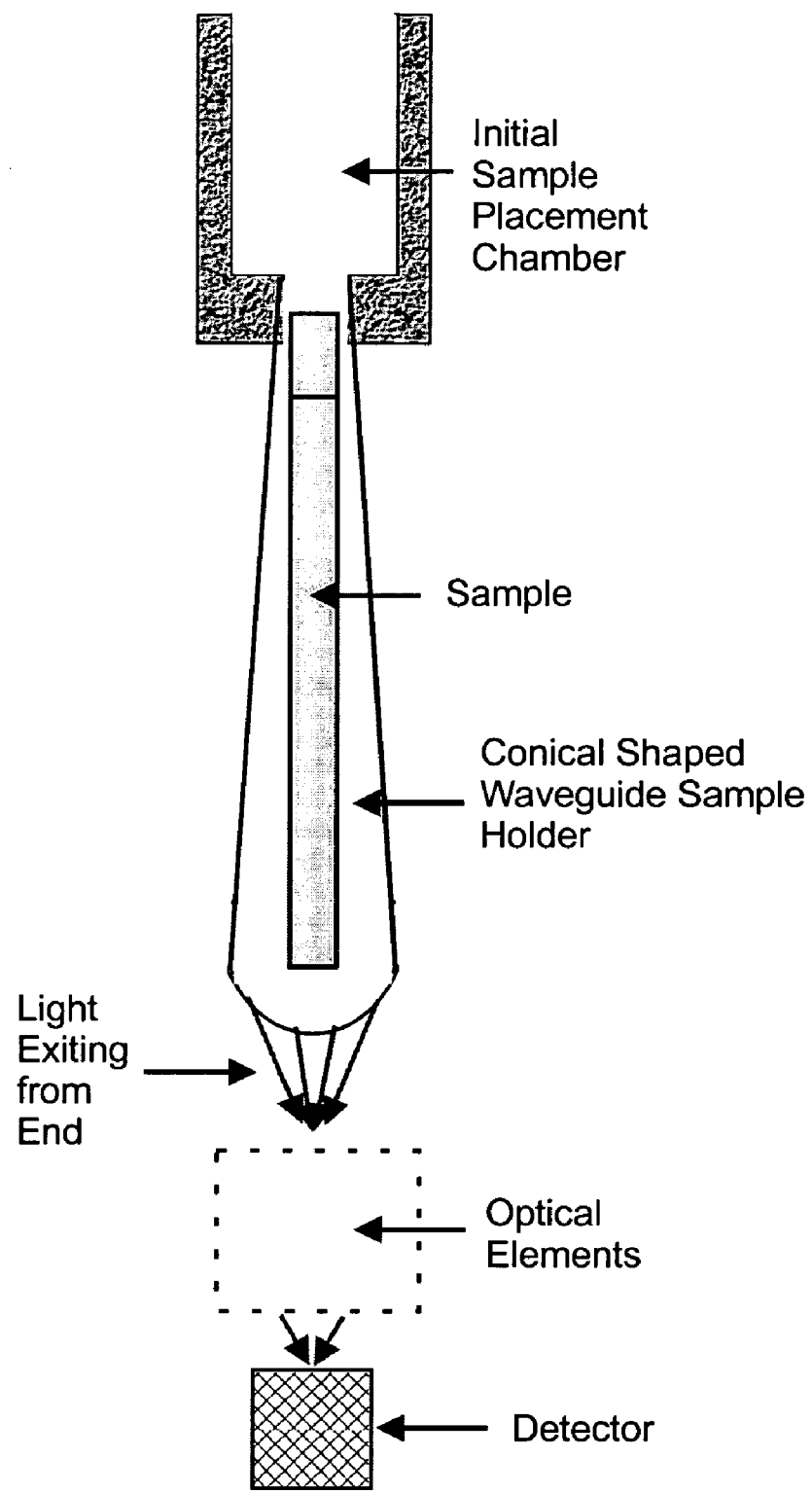
FIG. 5. Schematic side view of luminescent detection system, where the waveguide sample holder has conical shape.

The waveguide sample holder with a conical shape and a curved surface at the closed end to focus the emission light is shown in FIG. 5.

Figure 6:
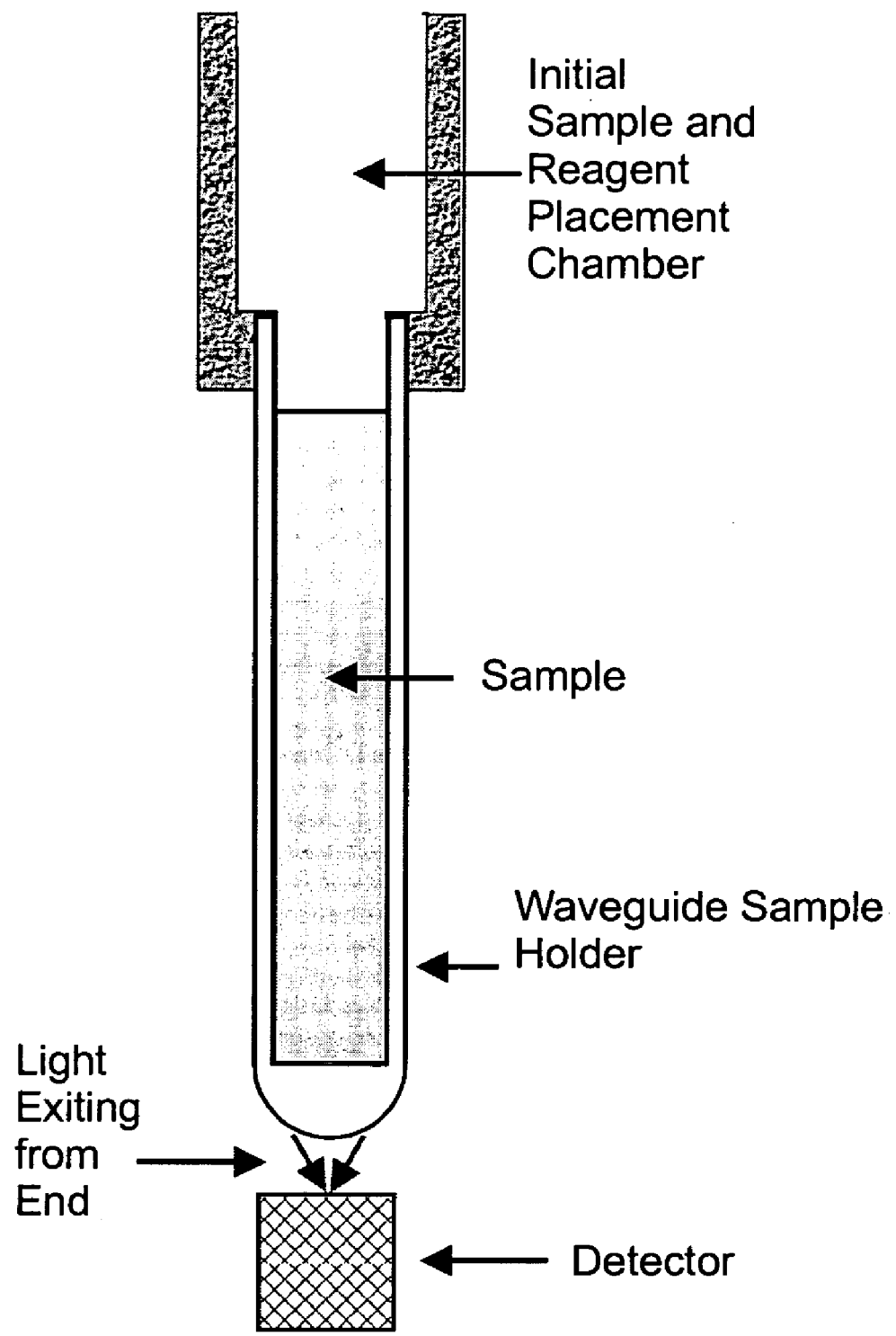
FIG. 6. Schematic side view of luminescent detection system, where there is no optical elements between the waveguide sample holder and the detector.

An arrangement where there are no optical elements between the waveguide sample holder and the detector can also be used, as shown in FIG. 6.

Figure 7:
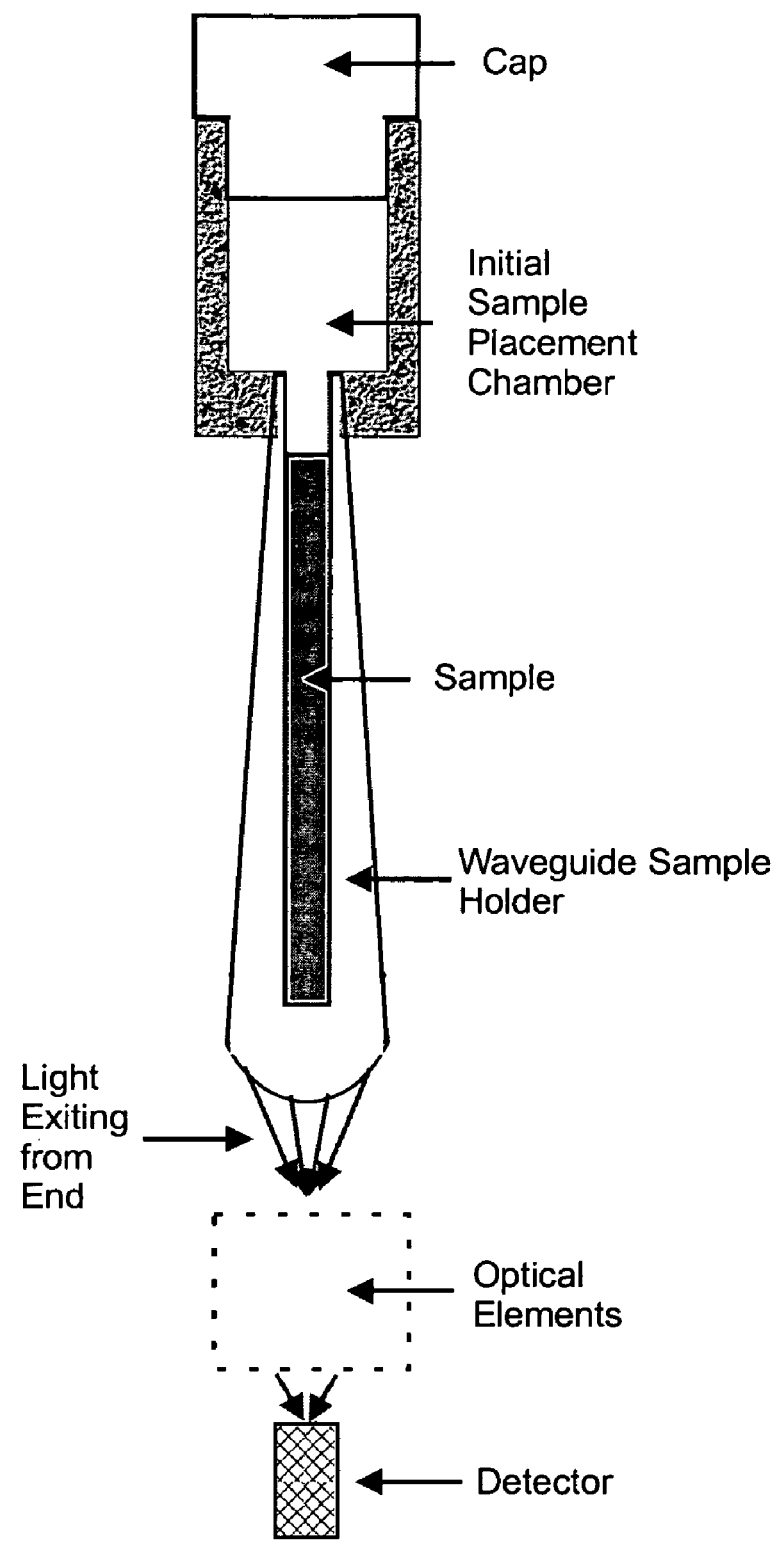
FIG. 7. Variation of the waveguide sample holder including a cap.

The waveguide sample holder may also include a cap. To allow addition of reagent(s), the cap can be removed before testing or it can have an inlet to allow the addition of reagent(s). This arrangement is shown in the exemplary embodiment of FIG. 7.

Figure 8:
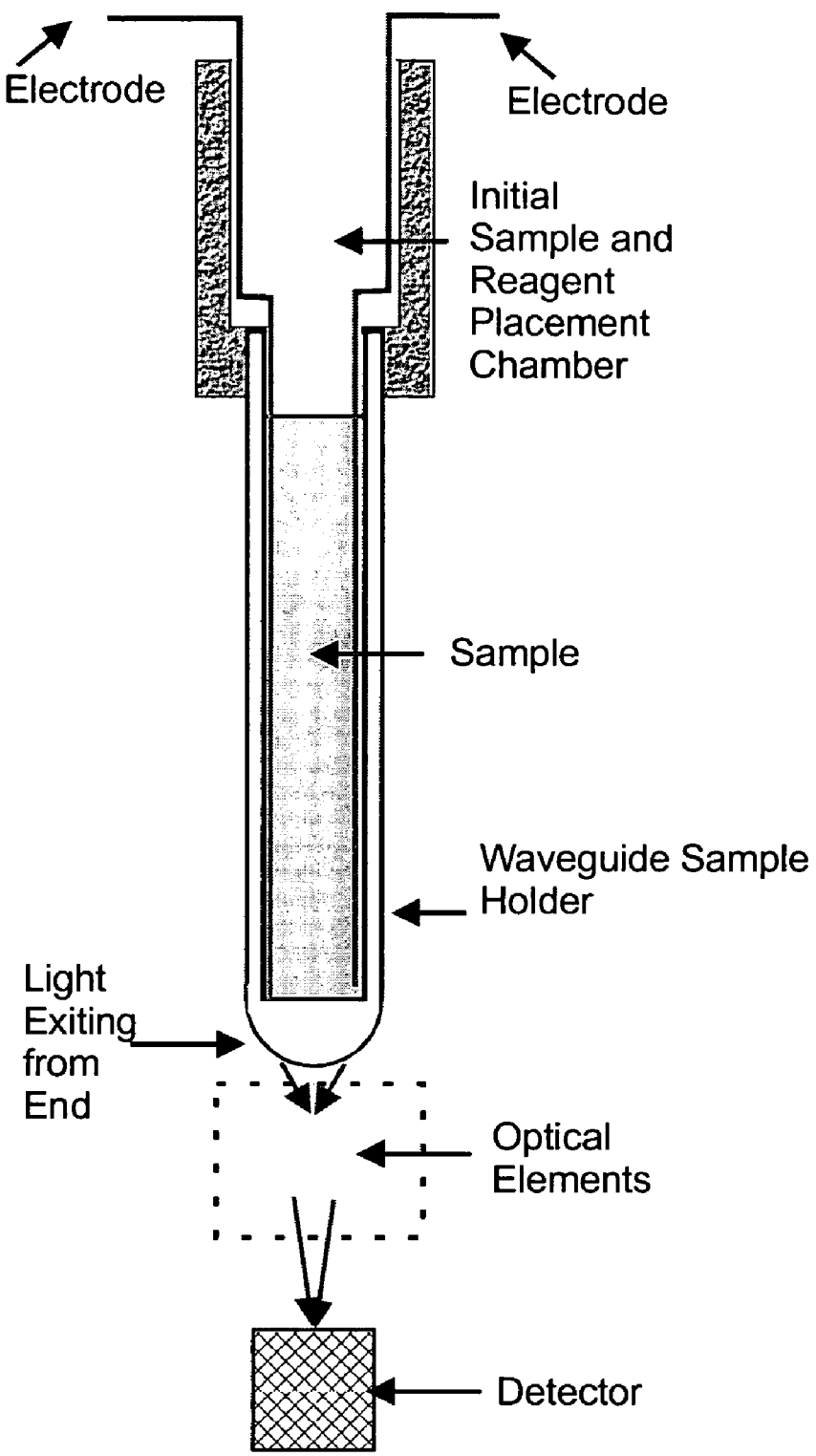
FIG. 8. Variation of the waveguide sample holder, where two electrodes are attached to the inside of the waveguide sample holder. When a voltage difference is applied between the two electrodes, electrochemiluminescence will follow.

Two electrodes can be attached to the inside of the waveguide sample holder. When a voltage difference is applied between the two electrodes, electrochemiluminescence can be activated and detected, as shown in FIG. 8.

Along the length of the waveguide sample holder, portions of the boundaries can be non-varying, and portions can be varying, substantially conically shaped for example.

Portions or the entire outer surface of the waveguide sample holder can be mirror or highly reflective, except at the light exit end of the waveguide sample holder. The waveguide sample holder can be made of any high index of refraction material, such as glass, plastic, etc. The waveguide sample holder can have portions that are uniform in cross-section and portions where the cross-section changes.

Figure 9:
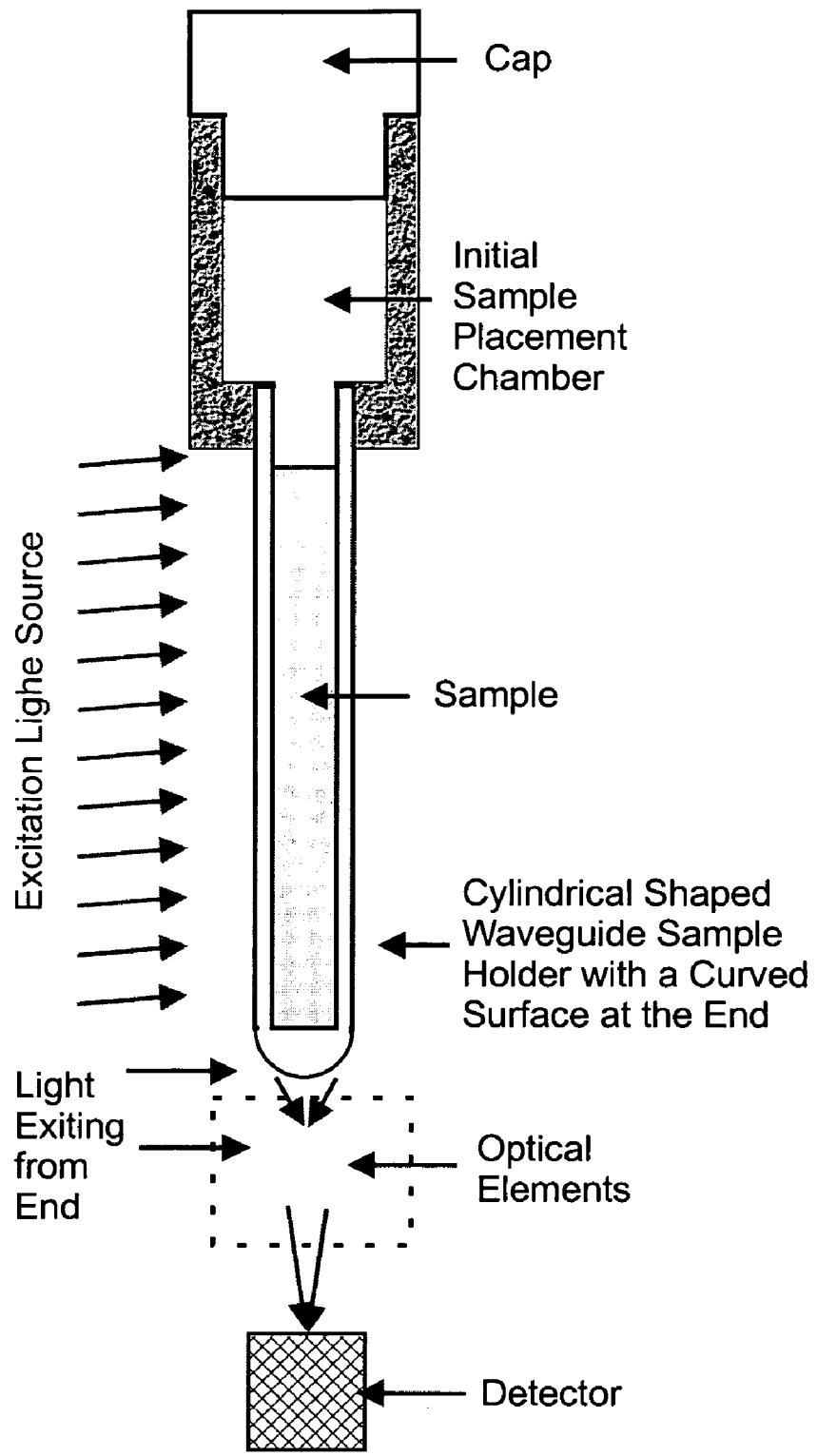
FIG. 9. Schematic side view of fluorescence/absorbance detection system, where the waveguide sample holder with the same cross sectional shape along the long axis and a curved surface at the end to focus the emission light passing through optical elements to a detector. There is a light source and optics to form the light. There can be a sample placement chamber and a cap.

In another embodiment, as shown in FIGS. 9-19 and 22-23, for fluorescence and absorbance applications, a fluorometer/photometer is provided that comprises one or more waveguide sample holders, one or more optical systems, one more excitation light sources and one or more optical detectors. The waveguide sample holder has a hollow region to hold the sample. The excitation light is introduced at an angle or perpendicular to one surface of the waveguide sample holder. The waveguide sample holder is made of material that can guide emission light to the closed end of the waveguide sample holder. There are one or more detectors that detect the emission light coming out of the closed of the waveguide sample holder. Schematic of waveguide sample holder with cylindrical wall is shown in FIG. 9.

The excitation light is incident nearly perpendicular to the surface, but with a slight tilt towards the sample placement chamber end of the waveguide sample holder.

There is a sample placement chamber on the end of the waveguide sample holder not used for detection.

There is a set of optical elements between the excitation light source and the waveguide sample holder to filter the excitation light, and form the shape of the excitation light and direct the excitation light to the waveguide sample holder.

There can be a set of optical elements to focus, guide or filter the emission light.

The detector can be one of the following: spectrometer, PMT, CCD, CMOS imaging arrays or photodiode, or any other optical detector.

The applications may comprise the following arrangements and design alternatives.

Figure 10:
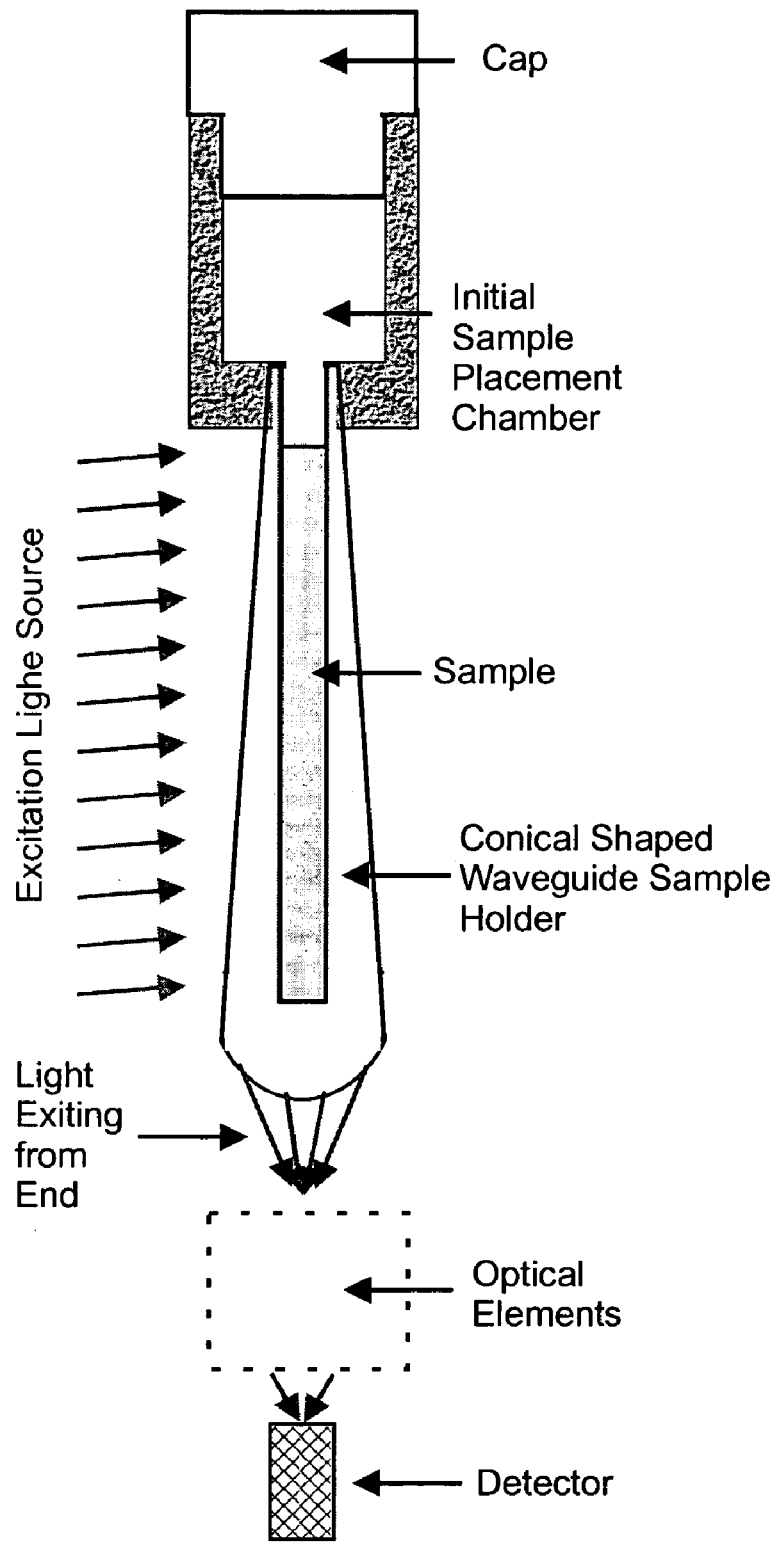
FIG. 10. Schematic side view of fluorescence/absorbance detection system, where the waveguide sample holder has a smaller cross sectional area on one end and a larger cross sectional area on the closed end.
Figure 11:
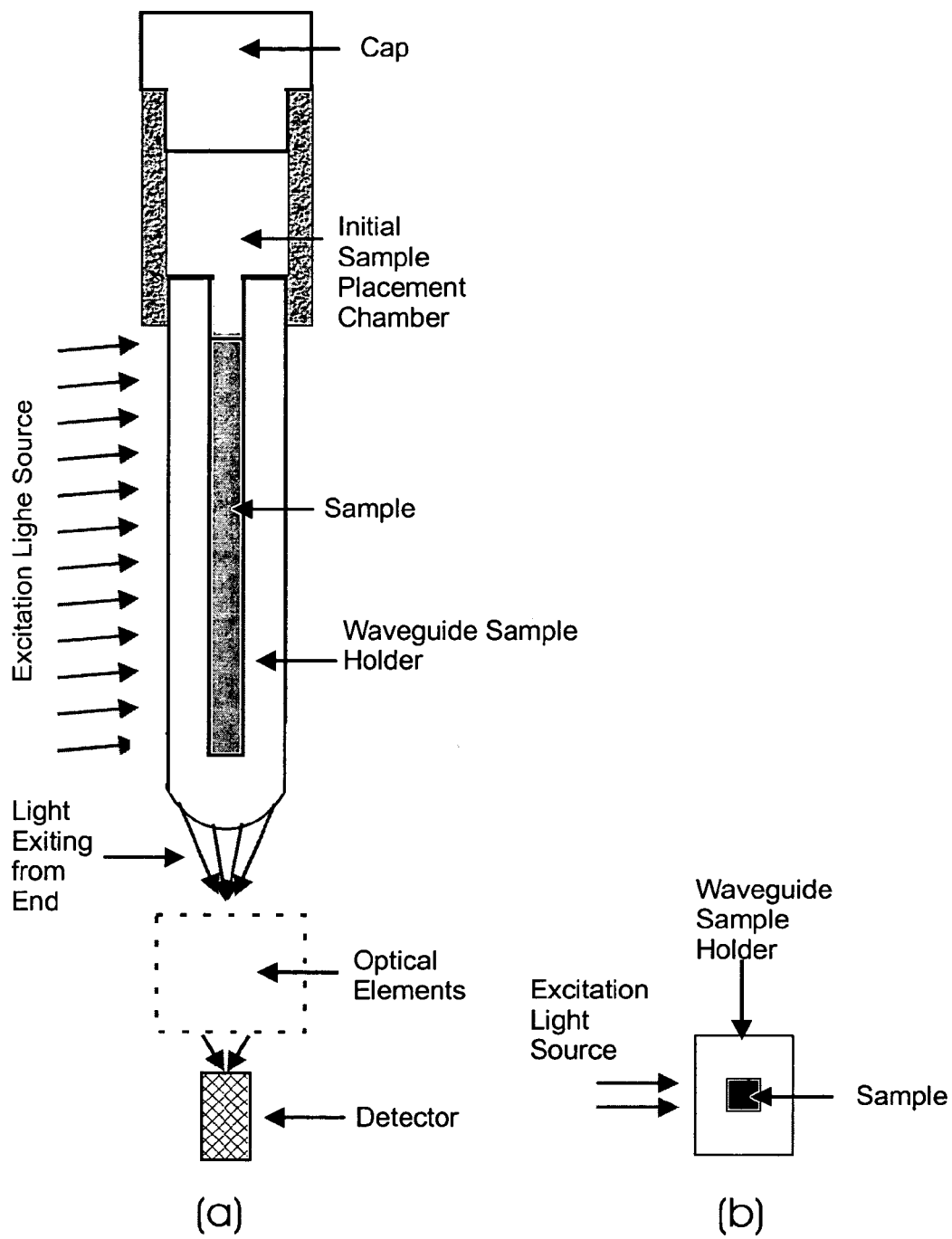
FIG. 11. (*a*) Schematic side view of fluorescence/absorbance detection system, where the waveguide sample holder has different cross sectional views: same cross sectional shape along the long axis is viewed from a direction shown in FIG. 11*a*, while different cross sectional shape along the long axis, smaller cross sectional area on the top and a larger cross sectional area on the bottom, is viewed from a direction rotated 90 degrees along the vertical axis, as shown in FIG. 10. (*b*) The cross sectional view of the waveguide sample holder.
Figure 12:
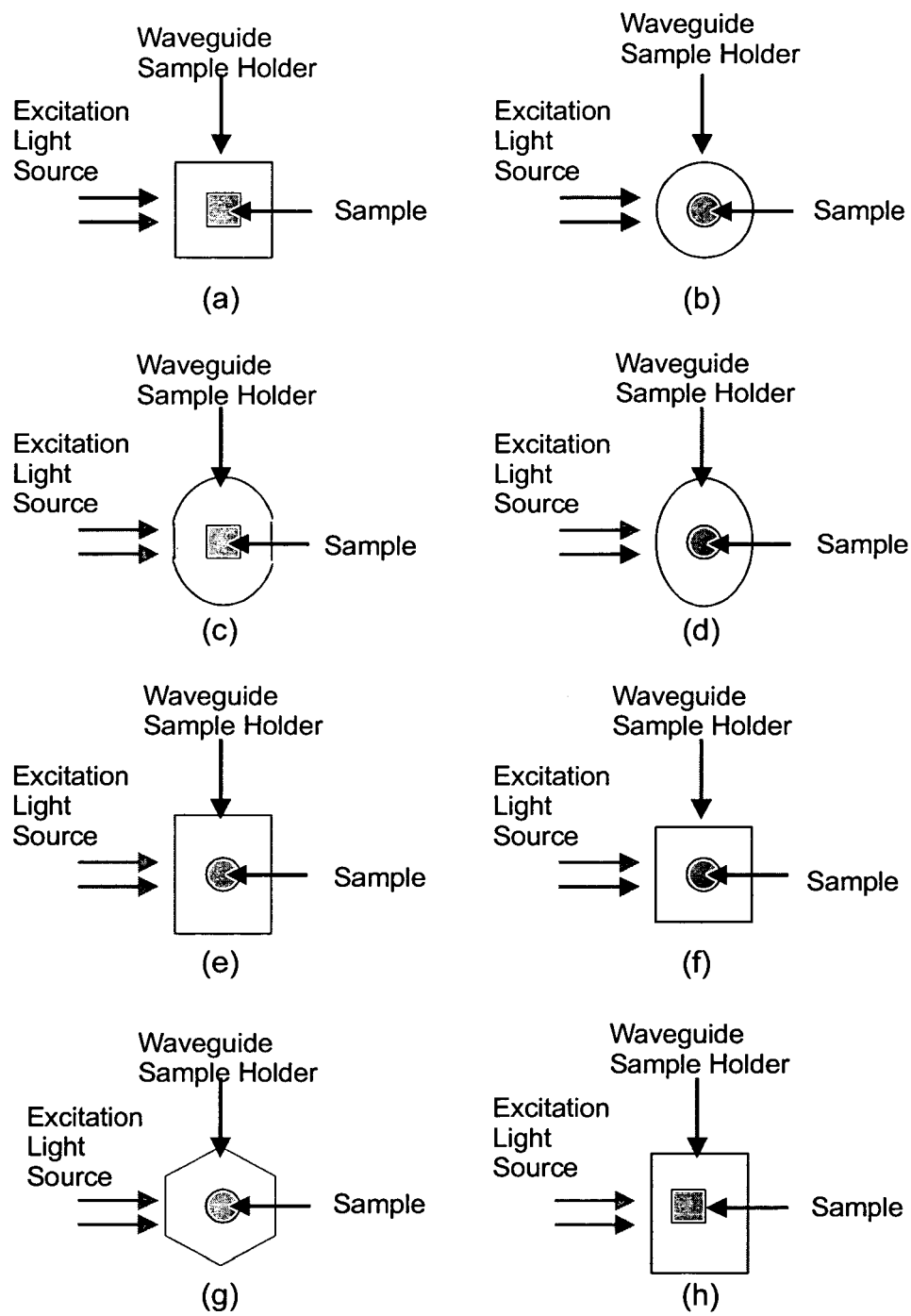
FIG. 12. Examples of cross sectional views of waveguide sample holders.

A waveguide sample holder with a conical shape is shown in FIG. 10. There is a curved surface at the large end to focus or collimate the emission light exiting the waveguide sample holder and to contain the sample.

For example, along the length of the waveguide sample holder, parts of the boundaries can be uniform and part can be varying. The outer surface of the waveguide sample holder that the light excitation light source impinges is parallel to the other surfaces in the side view, as shown in FIG. 11a. The side view shifted by 90 degrees is same as shown in FIG. 10, where the cross-sectional area of the top of the waveguide sample holder is smaller than that of the closed end.

The cross-sectional shape of the outer surface of the waveguide sample holder can be rectangular and the cross-sectional shape of the sample area can be square, as shown in FIG. 11b.

Various cross-sectional shapes of the outer surface of the waveguide sample holder and of the sample area are shown in FIG. 12a-h. The cross-sectional shape of the outer surface of the waveguide sample holder and the sample area are not limited to these geometries. Any shape that provides a good guide of light to the exit end of the waveguide sample holder can be used. The excitation light does not have to be perpendicular as shown in FIGS. 12a-h.

The cross-sectional shapes of the outer surface of the waveguide sample holder can have one shape, square for example, and the cross-sectional shape of the sample area can have a different shape, round for example, as shown in FIGS. 12c, d, e, f, g, and h.

Figure 13:
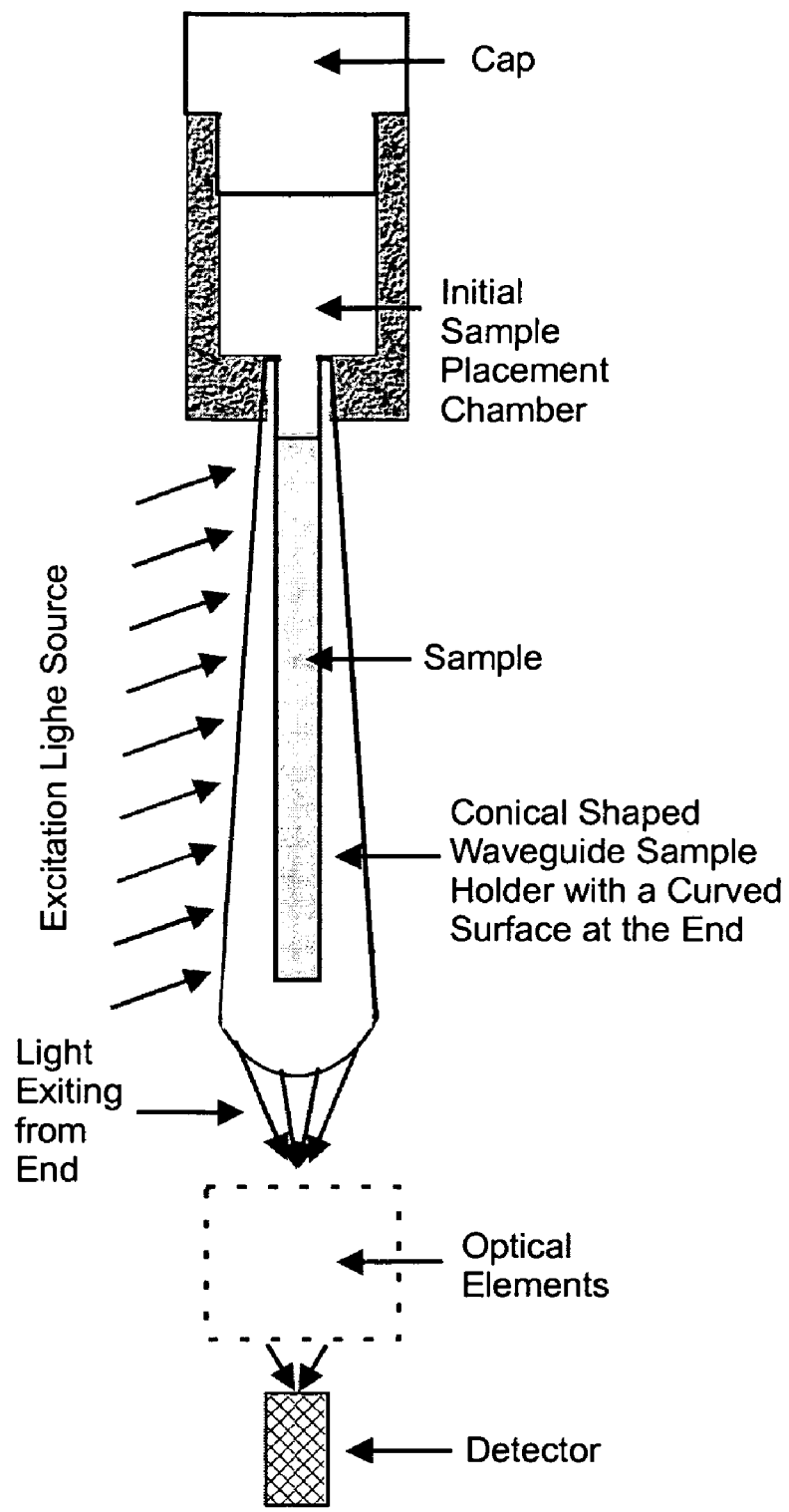
FIG. 13. The angle of the excitation light angle may be adjusted to minimize the excitation light entering the detector.

The outer shape of the waveguide sample holder has an axially symmetrical conical shape, as shown in FIG. 13. The excitation light must be incident at an angle relative to the surface such that it can enter the sample area, but not be reflected towards the detector.

Figure 14:
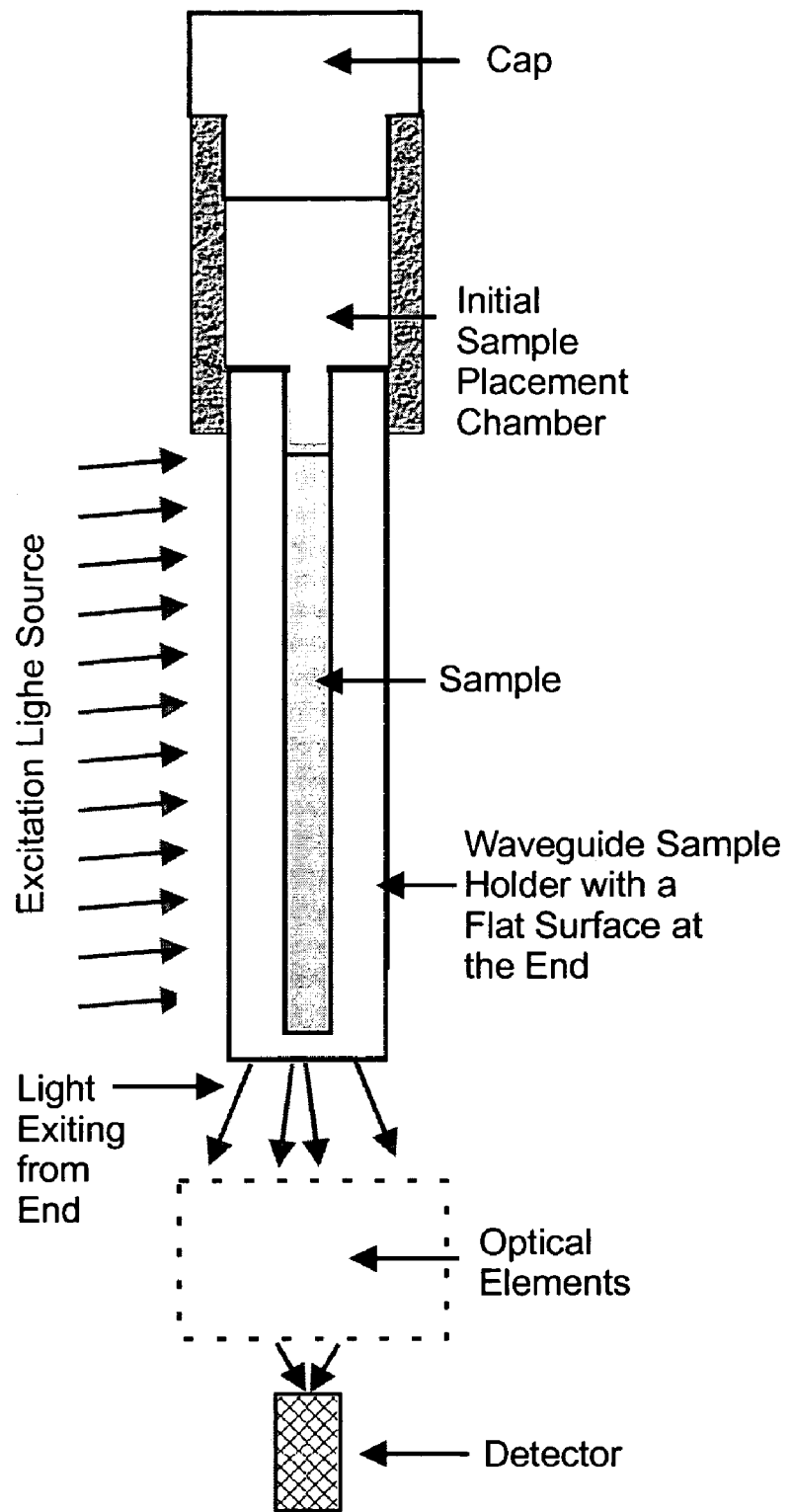
FIG. 14. Schematic side view of fluorescence/absorbance detection system, where the waveguide sample holder is flat at the end.
Figure 15:
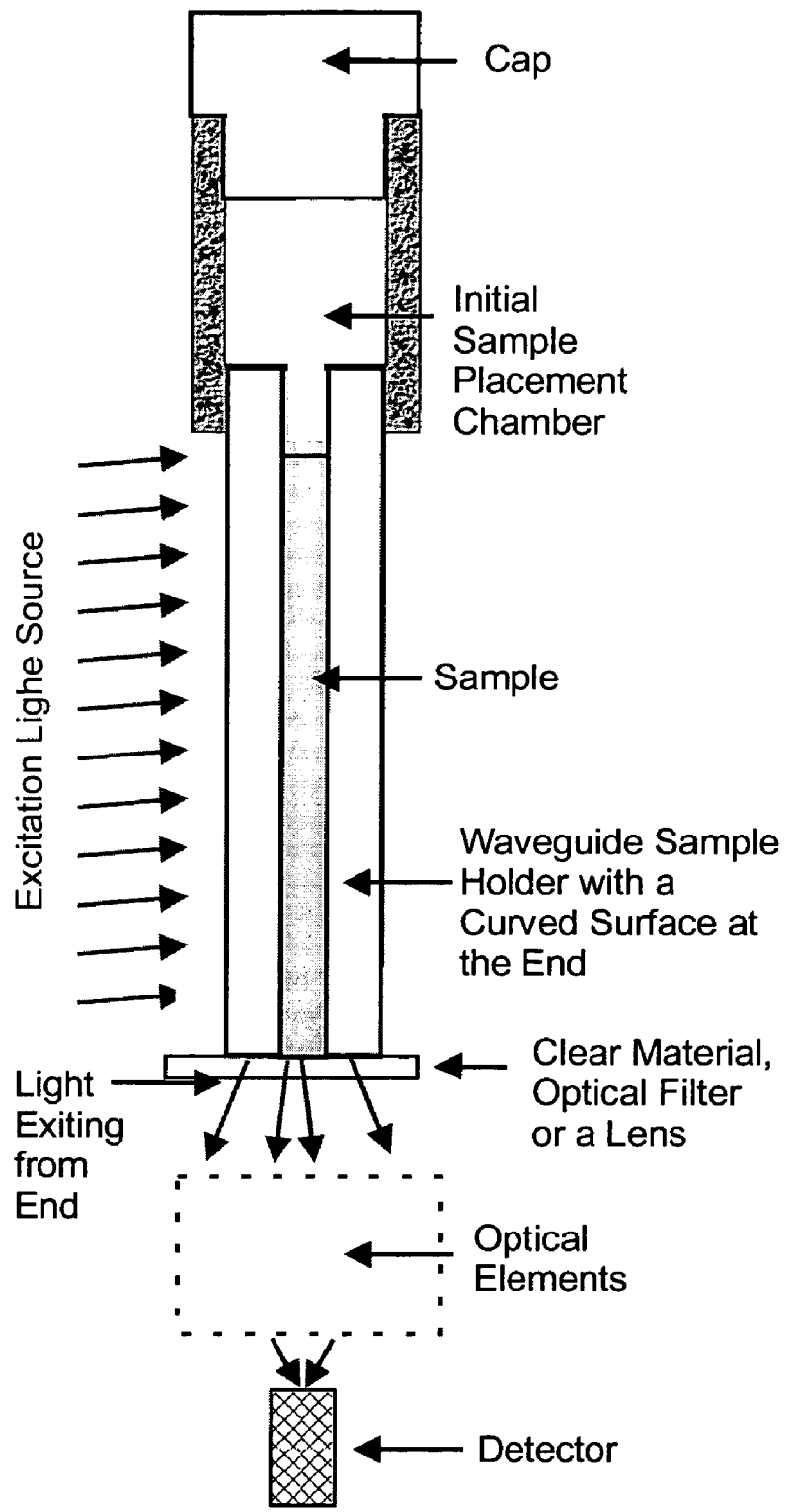
FIG. 15. Schematic side view of fluorescence/absorbance detection system, where the waveguide sample holder is open on both ends, and it can be placed in close proximity to a flat clear material (as shown in the drawing), an optical filter (not shown in the drawing) and/or a lens (not shown in the drawing).

The waveguide sample holder can have a flat surface at the end, as shown in FIG. 14.

The waveguide sample holder is open on both ends, and it can be placed in close proximity to a flat clear material (as drawn in FIG. 15), an optical filter (not drawn in figure), and/or a lens (not drawn in figure).

When there is a gap between the waveguide sample holder and the surface that separates the sample from the detector but contained by other walls, the sample can be allowed to flow. The detection of signal can be gathered periodically over the specified duration of the sample flow.

Figure 16:
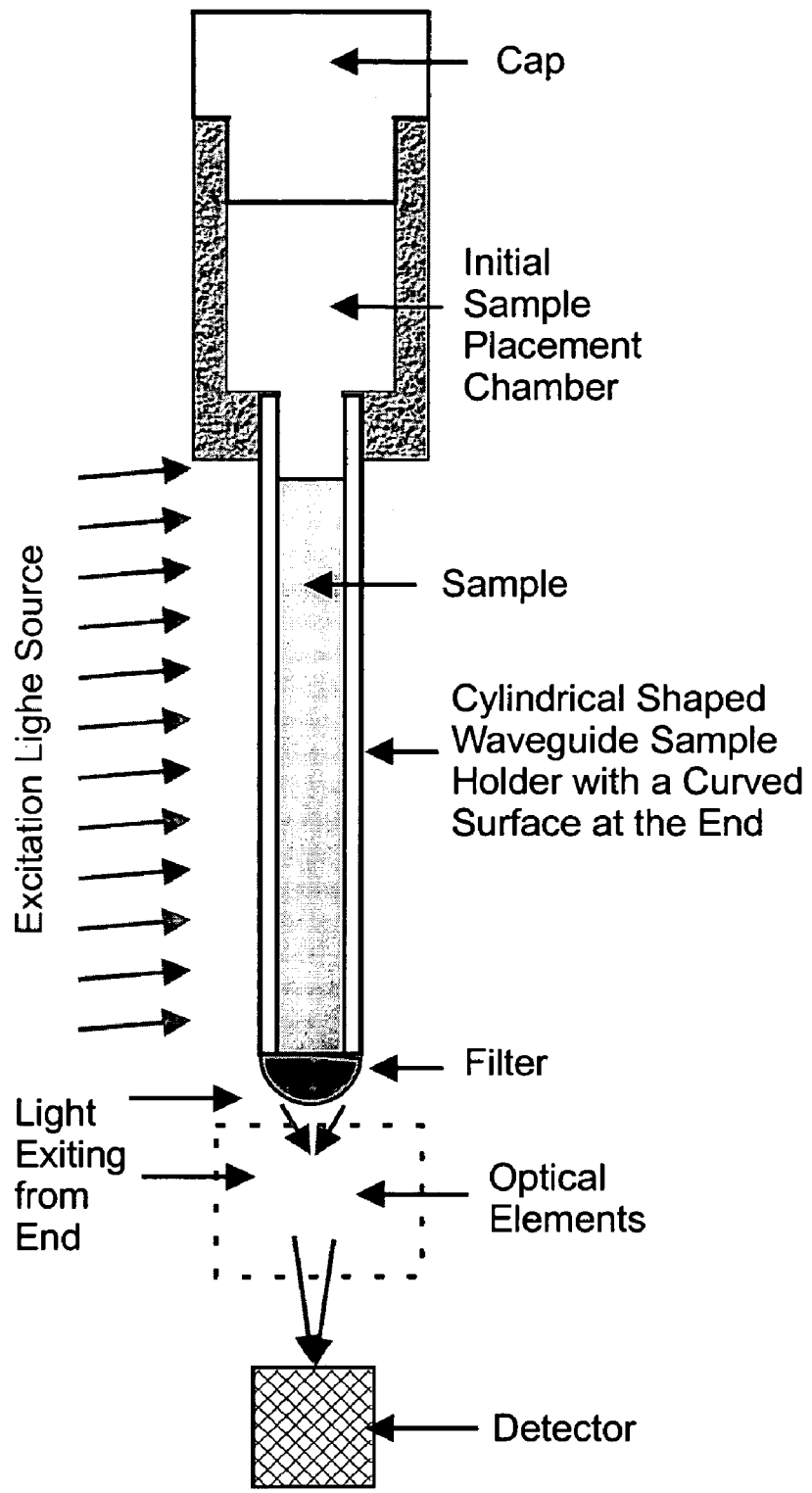
FIG. 16. Schematic side view of fluorescence/absorbance detection system, where the curved end of the waveguide sample holder is made of an optical filter material.

The curved section of the waveguide sample holder may be made of an optical filter material, so that the filter is combined together with the waveguide sample holder, as shown in FIG. 16.

Figure 17:
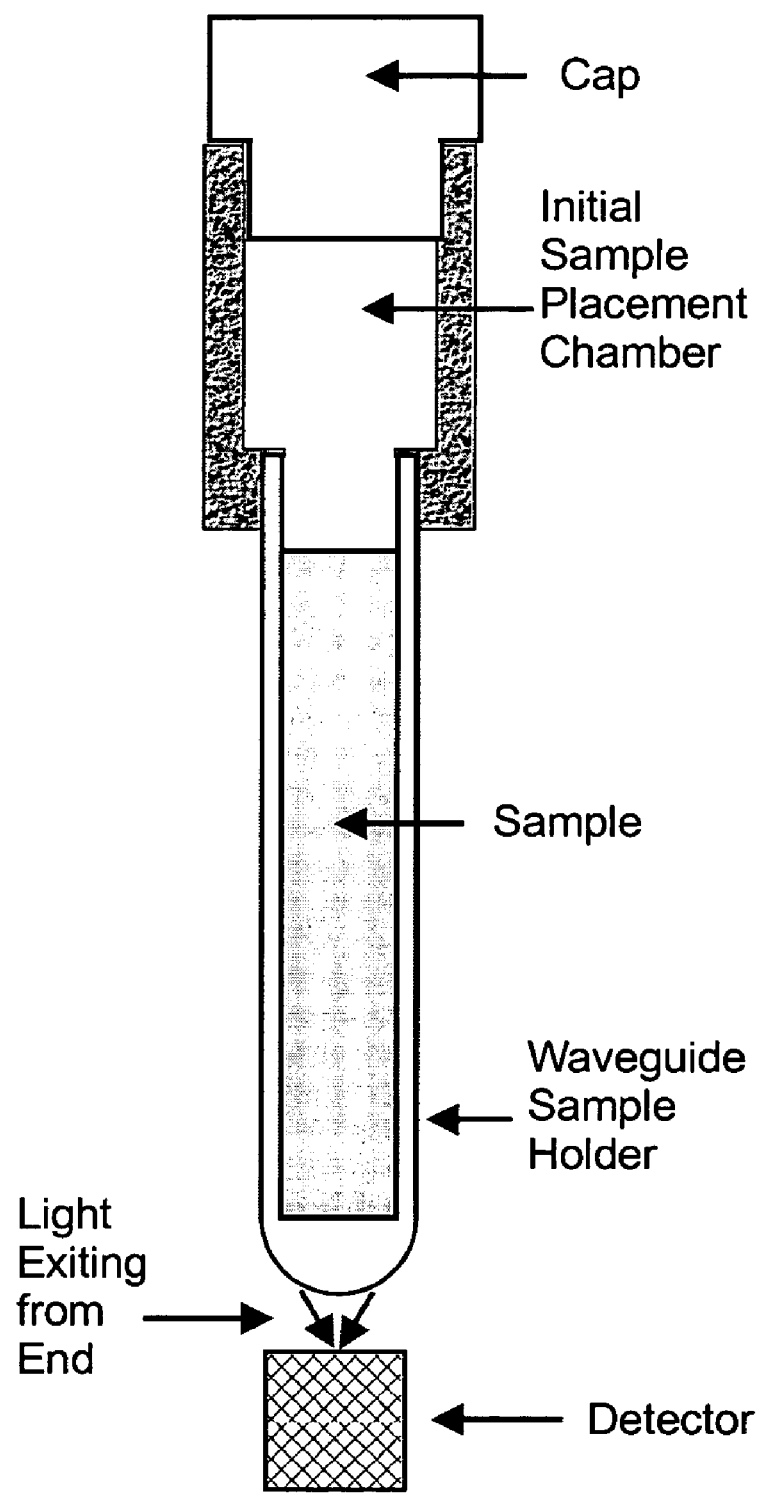
FIG. 17. Schematic side view of fluorescence/absorbance detection system, where there are no optical elements between the waveguide sample holder and the detector.

There may be no optical elements between the waveguide sample holder and the detector, as shown in FIG. 17.

Figure 18:
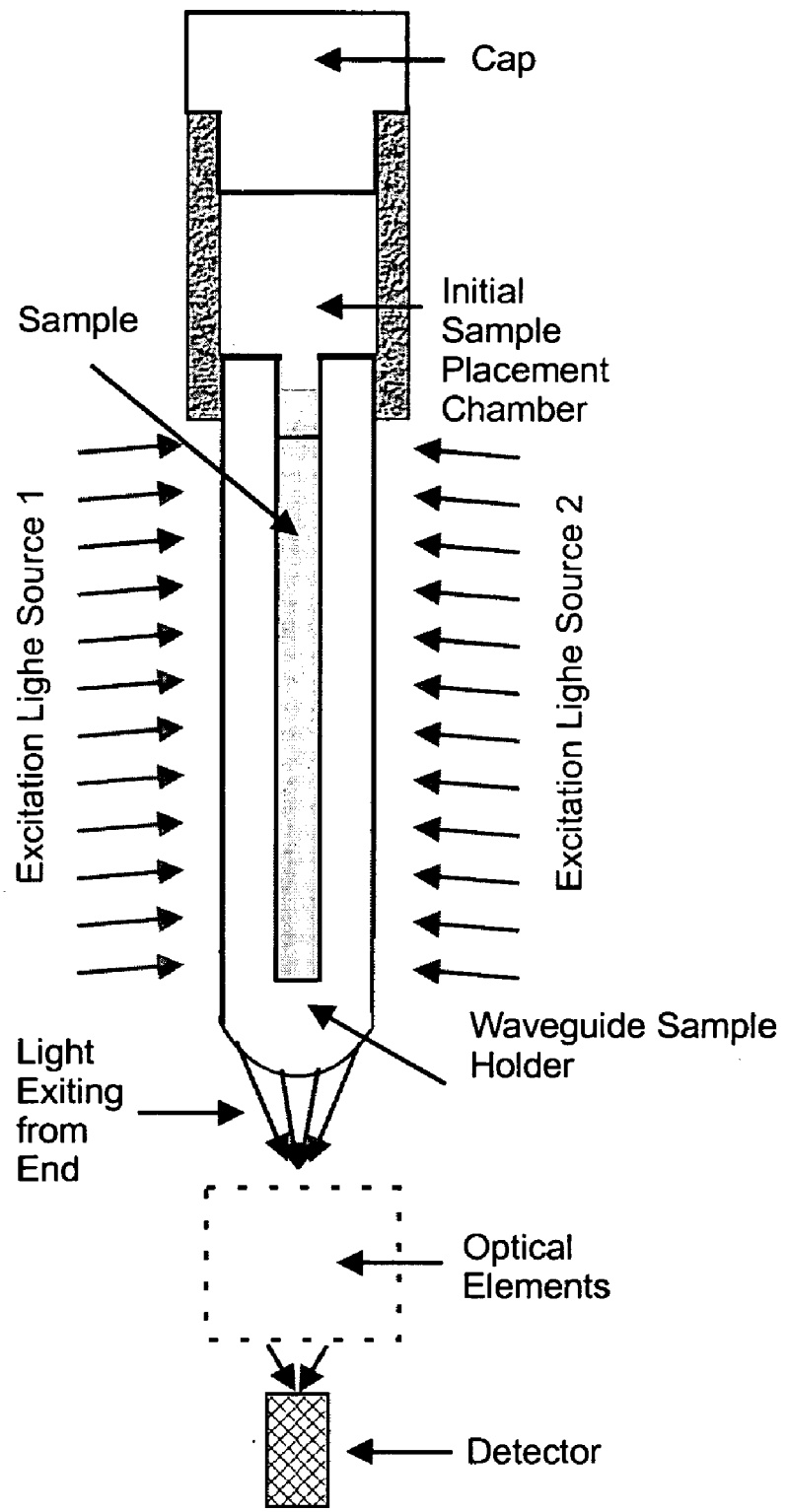
FIG. 18. Schematic side view of fluorescence/absorbance detection system, where two or more excitation light sources are used to excite the sample.

There can be one or more excitation light sources, as shown in FIG. 18.

Figure 19:
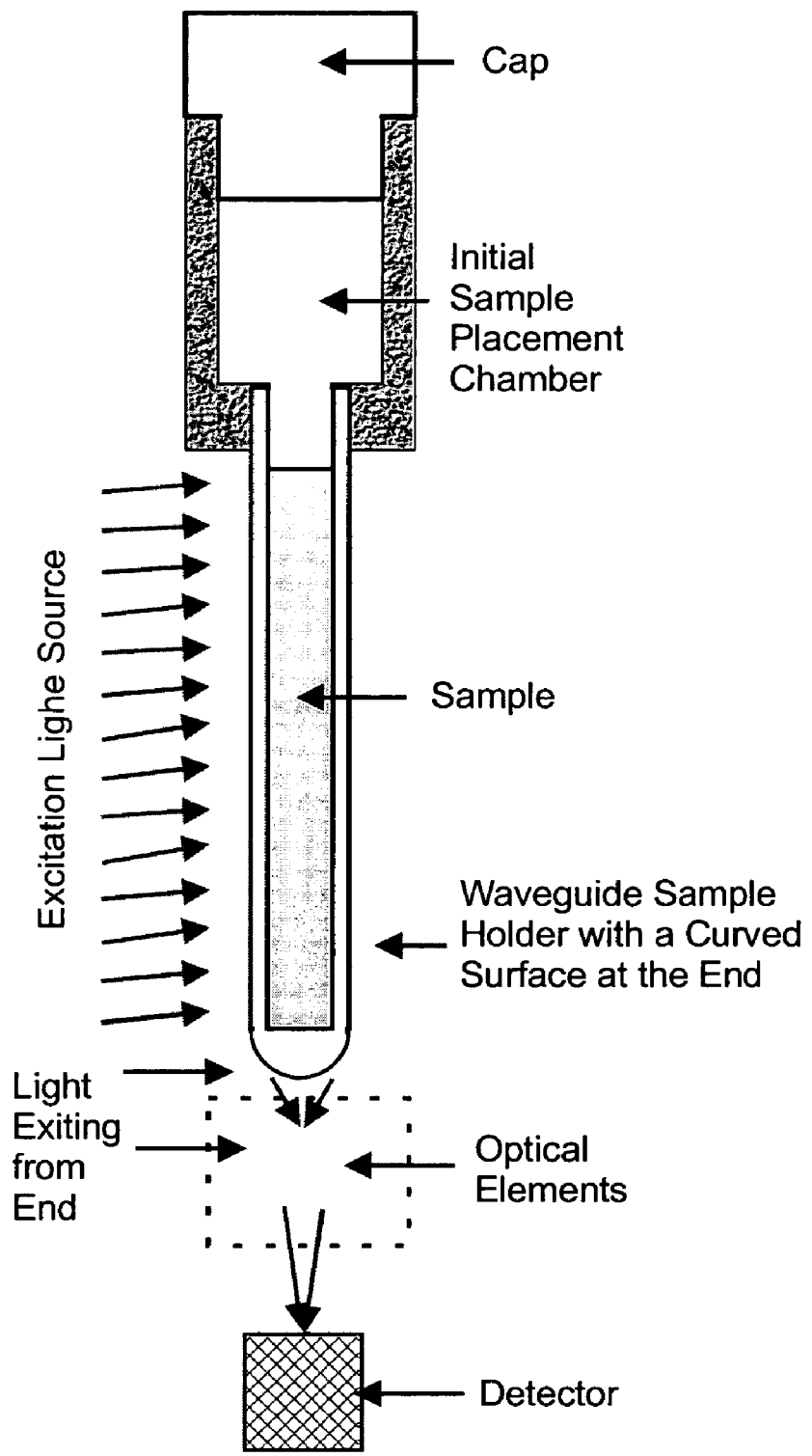
FIG. 19. Schematic side view of fluorescence/absorbance detection system, where the excitation light source is not collimated and need not be perpendicular to the surface of the waveguide sample holder.

The excitation light does not need to be parallel collimated, as shown in FIG. 19.

The waveguide sample holder can be made of any high index of refraction material, such as glass, plastic, etc.

The light source can be lasers, LEDs, arc lamps, incandescent lamps, etc.

One or more excitation light sources with same wavelength can be used.

One or more excitation light sources with different wavelengths can be used.

The excitation light can illuminate all or part of the sample.

The filters can be long pass, colored glass, dichroic filter or bandpass type of filters.

There can be one or more filters before the detector.

There can be one or more lenses before the detector.

The waveguide sample holder can have portions that are uniform in cross-section and portions where the cross-section changes.

The instrument can include more than one waveguide sample holder. It can also include a waveguide sample holder for reference.

Since the instrument can also detect the excitation light, absorbance of the excitation light by the sample and/or emission reagent can be detected and reported.

The sample can contain more than one fluorescent material, and the detection can be multiplexed using excitation of appropriate wavelengths and detector with appropriate filters to differentiate the signals associated with the various different emission wavelengths.

The signal for the luminescence and fluorescence can be read repeatedly in time.

The instrument will provide a temperature controlled environment for the waveguide sample holder. The temperature can be programmed to range between 0° C. and 100° C. For example, the temperature can be held at a constant value. For another application, the temperature can be ramped up to one value and changed to another value at a later time. For another application, the temperature can cycled between two temperatures. The temperature and the duration are to be programmed by the user.

For absorbance applications, an excitation source is used, but filters may or may not be needed between the waveguide sample holder and detector.

Figure 20:
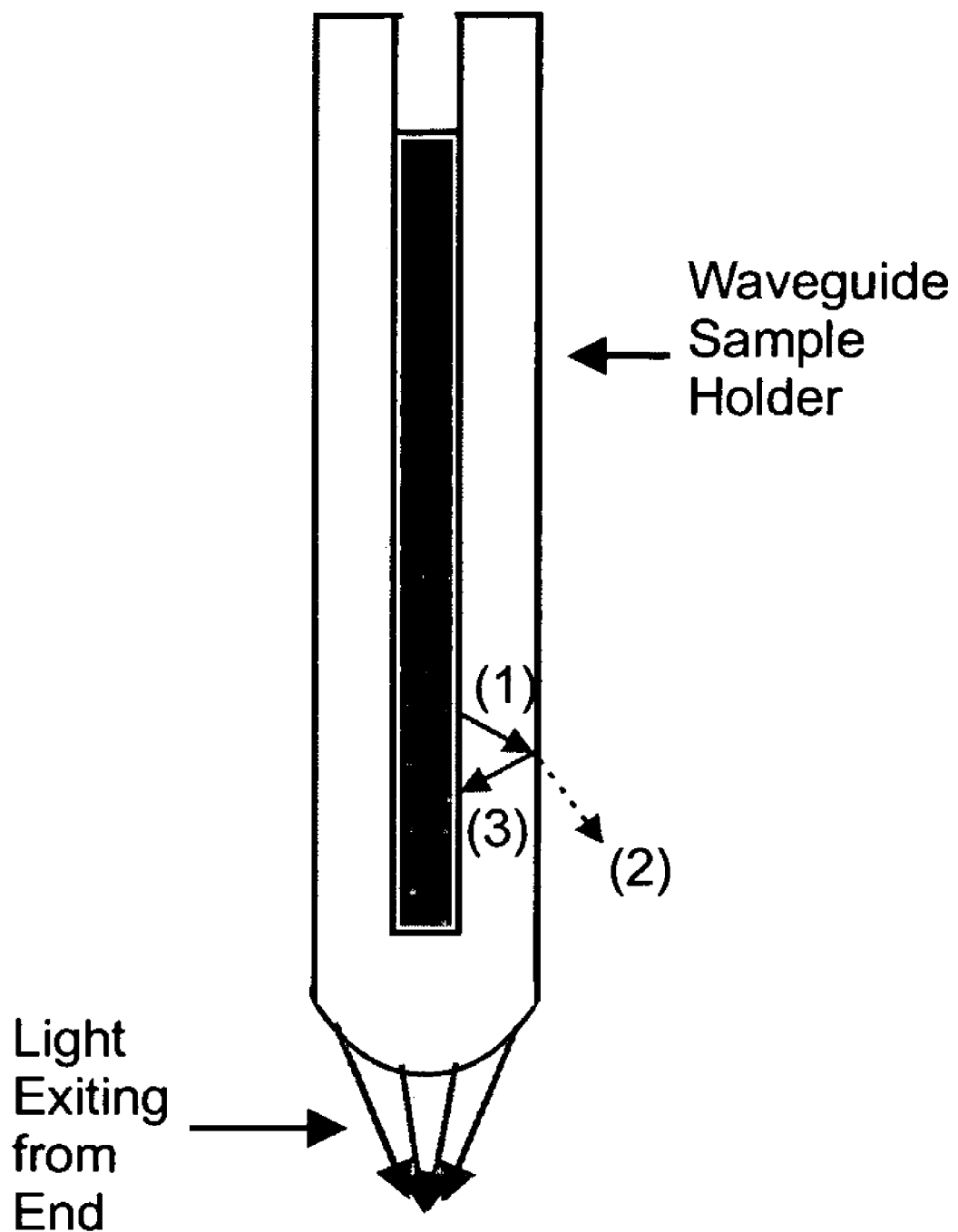
FIG. 20. Schematic showing the light signal propagation and reflection at the air and the waveguide sample holder interface for cylindrically shaped waveguide sample holder with same cross sectional shape.

The principle of the exemplary embodiments of the invention is that the emission light can be gathered efficiently into the detector using a waveguide sample holder designed as a light guide, and the limit of detection can be improved compared to conventional instruments and waveguide sample holders FIG. 20 shows the principle of detection of the emission signal at the end of the waveguide sample holder. Emission light, ray (1), impinges on the waveguide sample holder wall. If the angle of incidence is larger than the critical angle, all the light will be reflected internally within the waveguide sample holder, ray (3). If the angle of incidence is smaller than the critical angle, some of the light will be transmitted out of the waveguide sample holder, ray (2), and some will be reflected internally within the waveguide sample holder, ray (3). A portion of the emission light rays from the whole sample in the waveguide sample holder will exit at the end of the waveguide sample holder.

Figure 21:
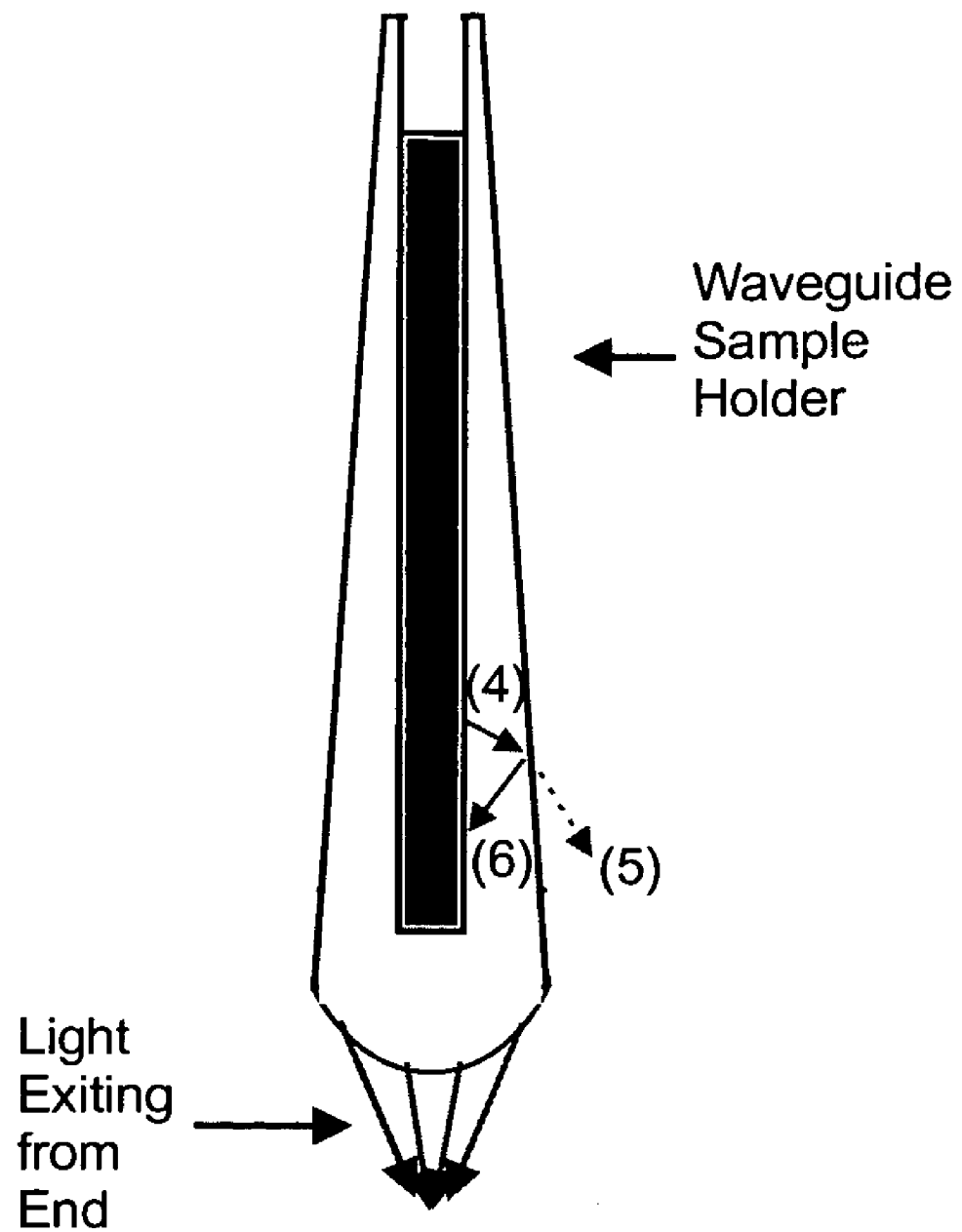
FIG. 21. Schematic showing the light signal propagation and reflection at the air and the waveguide sample holder interface for conically shaped waveguide sample holder.
Figure 22:
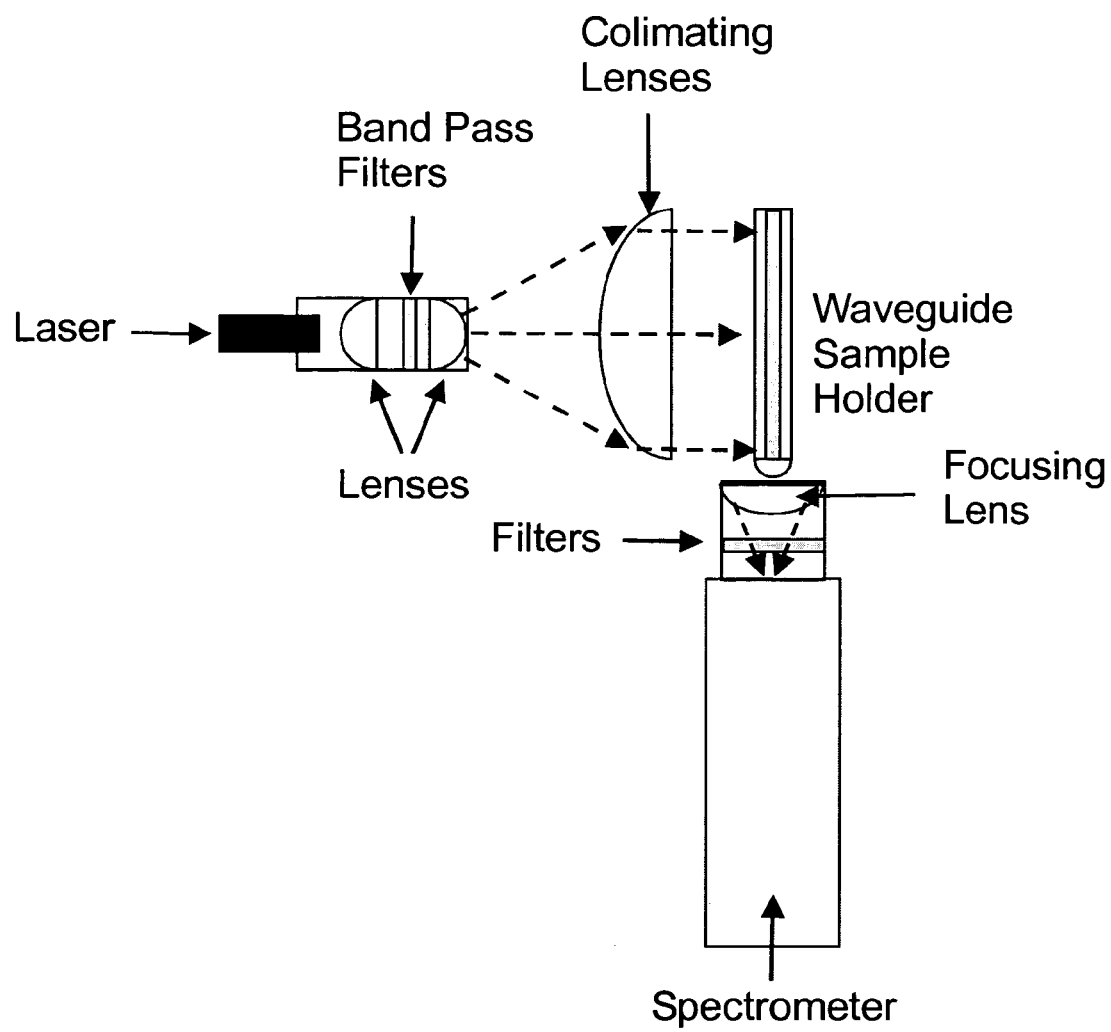
FIG. 22. Schematic of a specific implementation of the invention is an instrument that can be used as a fluorometer. The waveguide sample holder is a capillary tube with a lens at the end. The excitation light source is a laser. The signal is collected at the end of the waveguide sample holder. After focused by a lens and going through a filter, the light enters the spectrometer. The spectrometer gathers the signal of both the excitation wavelengths and emission wavelengths.
Figure 23:
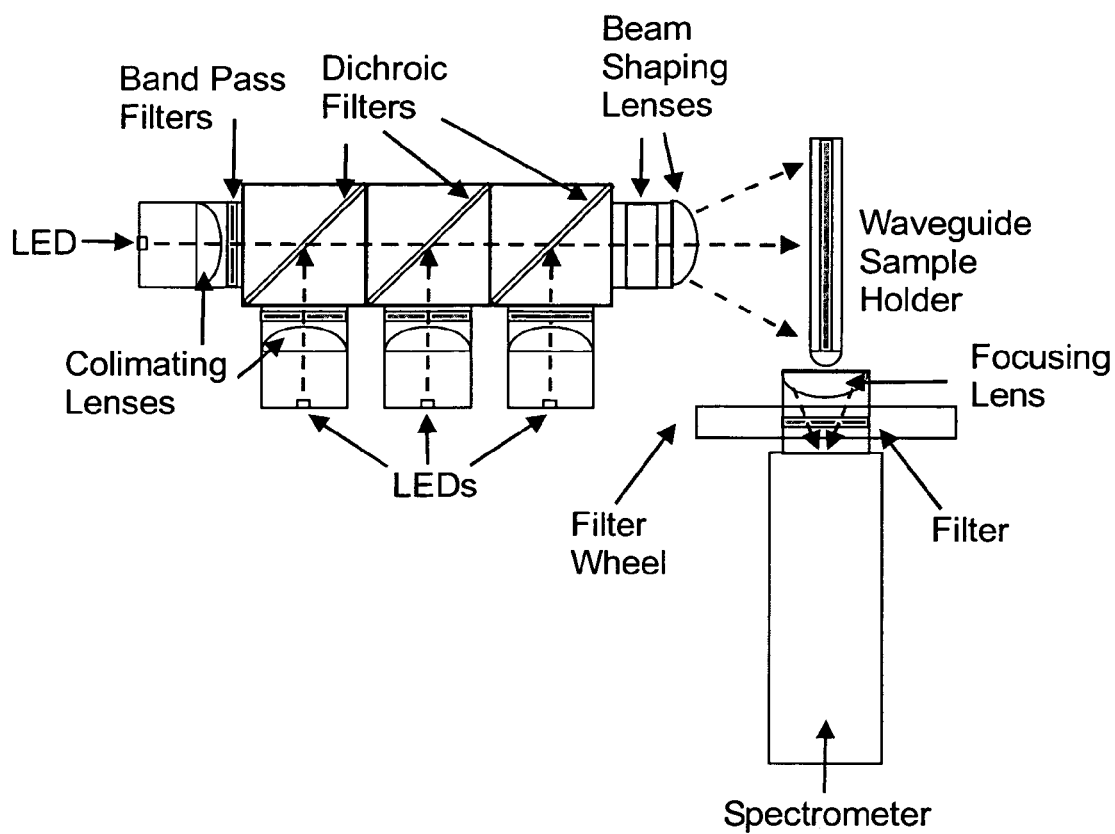
FIG. 23. Schematic of another specific implementation of the invention is an instrument that can be used as a luminometer, fluorometer and photometer. The waveguide sample holder is a capillary tube with a lens at the end. The excitation light source consists of set of four LEDs. The signal is collected at the end of the waveguide sample holder. After focused by a lens and going through a filter or set of filters in a filter wheel, the light enters the spectrometer. The spectrometer gathers the signal of both the excitation wavelengths and emission wavelengths.

Each time part of the light is transmitted out of the waveguide sample holder, ray (2), there is a loss of light and a reduction of the emission signal that arrives at the detector. The loss can be minimized by the use of waveguide sample holder walls of optimum thickness or the use of conical shape, because both of these features will lead to a reduced number of reflections before the emission light exits at the end of the waveguide sample holder. FIG. 21 illustrates the use of conically shaped waveguide sample holder. Again, if the angle of incidence of emission light is larger than the critical angle, all the light will be reflected internally. If the angle of incidence of the emission light, ray (4), is smaller than the critical angle, some of the light will be transmitted out of the waveguide sample holder, ray (5), and some will be reflected internally within the waveguide sample holder, ray (6). The reflected ray (6) will travel a longer distance before it will encounter another external waveguide sample holder surface, resulting in less loss than for a waveguide sample holder with parallel walls. A larger portion of the emission light rays from the whole sample in the waveguide sample holder will exit at the end of the waveguide sample holder. This might provide an improved signal than for a waveguide sample holder with parallel walls.

For fluorescence applications, the excitation light at the detector should be minimized, and that can be accomplished by illuminating the excitation light along the waveguide sample holder at a perpendicular or nearly perpendicular angle. This causes the excitation light entering the waveguide sample holder to be essentially lost through transmission out the waveguide sample holder walls as a result of the high (nearly 90 degrees) angle of incidence and the large number of reflections. Thus, only a small amount of reflected excitation light will exit at the end of the waveguide sample holder. The use of optical filtering techniques can further reduce the level of excitation light detected at the end of the waveguide sample holder.

Examples of Implementation

Two specific implementations of the liquid phase Integrating Waveguide Sensor invention and its experimental data are described below. The first embodiment of the invention is a fluorometer that utilizes a laser as the excitation light source. A lens is used to produce parallel light through a laser clean-up filter. The laser light is fanned out, followed by collimation before the laser light impinges on the waveguide sample holder. The emitted fluorescent light is collected at the end of the waveguide sample holder. It is detected by a spectrometer, after focused by a lens and passing through a filter. The signal can be collected once or collected repeatedly over a prescribed period. The instrument can be designed to detect a number of samples and a reference in one procedure.

A second embodiment of the invention is a combined luminometer, fluorometer and photometer instrument that utilizes light emitting diodes (LEDs) as the excitation light source. The light from each LED is collimated by a lens into parallel rays. The filter allows a band of wavelength of the LED emission to pass and significantly reduce the transmission of radiation outside the band. This band of wavelength is directed towards the waveguide sample holder via a set of dichroic filters and a set of beam shaping lenses to produce illumination on the waveguide sample holder at nearly a 90 degree angle of incidence to the surface of the waveguide sample holder. The LEDs are arranged in the sequence of longer to shorter wavelength corresponding to left to right in FIG. 23. The dichroic filters allow the reflection of the wavelength of interest and transmit the longer wavelengths in the configuration shown in FIG. 23. After exiting the dichotic filters, the LED light is shaped using lenses to match the shape of the waveguide sample holder. A set of four LEDs allows the use of at least four different dyes. The emitted and excitation light are collected at the end of the waveguide sample holder. The light is detected by a spectrometer after focused by a lens and passing through a filter or a set of filters mounted in a filter wheel.

To use this second embodiment of the instrument as a luminometer, the LEDs will not be illuminated, and the filter wheel can be rotated to a position of no filter. After placing the sample and reagent into the waveguide sample holder, the luminescence signal is collected. The signal can be collected once or collected repeatedly over the duration of luminescence.

To use this second embodiment of the instrument as a fluorometer, four fluorescent dyes can be detected within the same waveguide sample holder. For example, the LEDs can provide excitation wavelengths of 630 nm, 590 nm, 530 nm, and 470 nm. The filter wheel will include long pass filters corresponding to the LEDs. The spectrometer collects light over a range from, for example, 400 to 750 nm. Four fluorescent dyes that can be excited in sequence by turning on one LED at a time with the appropriate selection of filter in the filter wheel. The appropriate signal is obtained in the wavelength region corresponding to the emission reagent.

To apply this second embodiment of the instrument as a photometer, absorbance of excitation light by the sample is obtained by comparing the result of the sample with a reference in the wavelength region of the LED. The appropriate LED can be turned on, but no filter may be needed in the filter wheel to allow the LED light to reach the spectrometer. Data will also be collected from a reference sample to obtain the amount of absorbance.

The second embodiment of the instrument can be designed to detect a number of samples and a reference in one procedure.

The second embodiment of the instrument can be designed to include temperature control to allow performance of an assay in environment other than the ambient temperature. For example a Positive Temperature Coefficient (PTC) thermistor can be used in the vicinity of the sample holder to control the temperature of the sample. As will be understood by skilled artisans the operation of the PTC thermistor can computer controlled. Some common applications requiring temperature control are given below. For example, the temperature can be held at 37° C. to keep cells alive and reproducing. For a second example, the temperature can be programmed to go to 95° C. to change double strand DNA to single strand. When this is followed by maintaining at approximately 65° C., isothermal DNA amplification can be achieved using appropriate reagents. For a third application, the temperature can be cycled between approximately 95° C. and 65° C. for DNA amplification using appropriate reagents.

The second embodiment of the instrument can be designed to include alternative LED wavelengths, and/or a greater or lesser number of LEDs.

Figure 24:
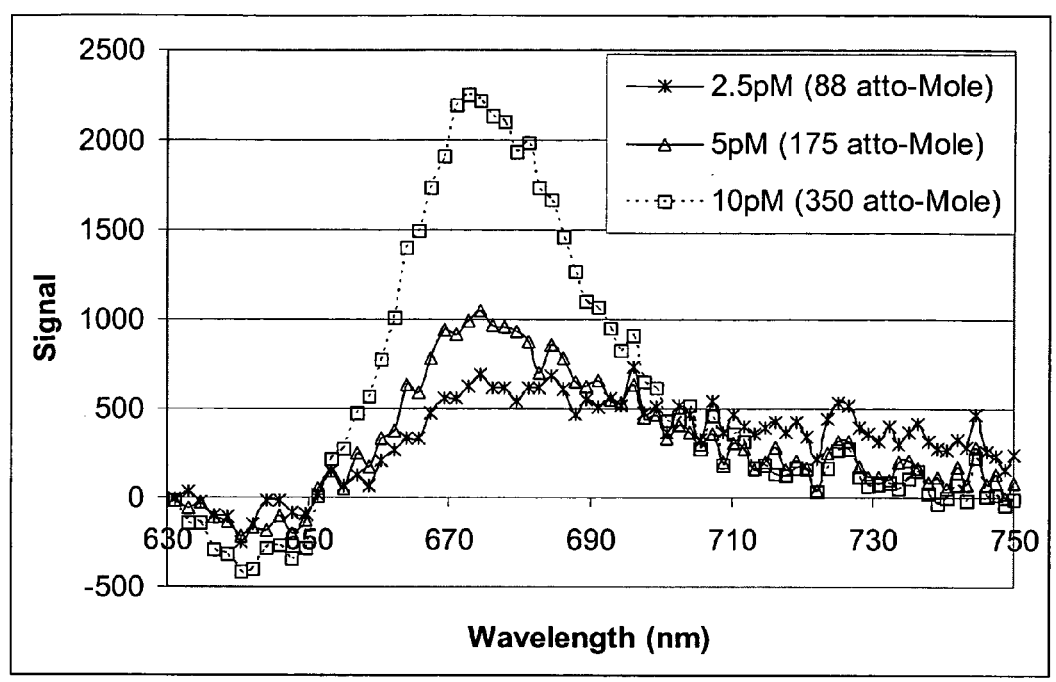
FIG. 24. Experimental data obtained using Cy5 fluorescent dye in the waveguide sample holder containing 35 microliters of sample using the LED instrument described in FIG. 23.

The second embodiment of the instrument was constructed. An example of the experimental data for detection of Cy5 fluorescent is shown in FIG. 24. The signals shown are after subtracting background and demonstrate that the liquid phase of the Integrating Waveguide Sensor can detect a 2.5 picomolar Cy5 dye concentration in a 35 microliter sample volume, or 0.088 femtomole of Cy5 dye.

While the invention has been shown and described with reference to certain exemplary embodiments thereof, it will be understood by those skilled in the art that various changes in form and details may be made therein without departing from the spirit and scope of the invention as defined by the appended claims.

We claim:

1. A sample holder comprising:
    a chamber for accommodating a sample therein;
    a distal end providing a first access to the chamber; and
    a proximal end comprising at least a light permeable portion; and
    at least one wall extending from the proximal end to the distal end in a longitudinal direction;
    wherein the chamber comprises an inner longitudinal surface and an outer longitudinal surface defined by the at least one wall,
    the inner longitudinal surface comprises a first cross-sectional shape when viewed in a plane perpendicular to the longitudinal direction;
    the outer longitudinal surface comprises a second cross-sectional shape when viewed in the plane perpendicular to the longitudinal direction; and
    the at least one wall comprises a waveguide configuration for directing light, which enters the chamber through the outer longitudinal surface, toward the proximal end.

2. The sample holder of claim 1, wherein the at least one wall comprises an annular wall.

3. The sample holder of claim 2, wherein the annular wall comprises a tapered shape in a form of a frustum of a cone tapering in the longitudinal direction toward the distal end.

4. The sample holder of claim 2, wherein the annular wall comprises a cylindrical shape in the longitudinal direction.

5. The sample holder of claim 1, further comprising a plurality of connected walls extending in the longitudinal direction from the distal end to the proximal end, wherein the inner longitudinal surface and the outer longitudinal surface are defined by the plurality of the connected walls.

6. The sample holder of claim 1, wherein at least one of the first cross-sectional shape and the second cross-sectional shape comprises at least one of a polygon and a continuous curve.

7. The sample holder of claim 1, at least one of the first cross-sectional shape and the second cross-sectional shape is axially symmetric with respect to a longitudinal axis of the chamber.

8. The sample holder of claim 1, wherein at least one of the first cross-sectional shape and the second cross-sectional shape comprises at least a portion configured to facilitate passage of excitation light through the at least one wall.

9. A system comprising the sample holder as claimed in claim 1, the system further comprising at least one light source configured for selectively illuminating the sample within the chamber through the outer longitudinal surface.

10. The system as claimed in claim 9, wherein the at least one light source comprises at least one of a laser, an LED, an arc lamp and an incandescent lamp.

11. The system of claim 9, wherein the light source is configured to emit light for illuminating the chamber at an angle of approximately 90 degrees with respect to the outer longitudinal surface of the chamber.

12. The system of claim 9, further comprising at least one optical element configured with respect to the at least one light source and the chamber to facilitate at least one of filtering, guiding and focusing the light emitted from the at least one light source toward the chamber.

13. The system of claim 12, further comprising a detector for detecting a light which has been at least one of focused, guided and filtered by at least one optical element.

14. The sample holder of claim 1, wherein the proximal end is integrally formed with the at least one wall.

15. The sample holder of claim 1, wherein the proximal end comprises a first surface and a second surface, and the chamber comprised an inner proximal surface defined by the first surface of the proximal end, and an outer proximal surface defined by the second surface of the proximal end.

16. The sample holder of claim 15, wherein the second surface of the proximal end comprises a curved portion for facilitating focusing of light permeating through the proximal end.

17. The sample holder of claim 15, wherein the first surface of the proximal end comprises an essentially flat portion.

18. The sample holder of claim 1, further comprising a placement chamber configured at the distal end.

19. The sample holder of claim 18, further comprising a cap removably configured with respect to the placement chamber for selectively blocking the first access to the chamber.

20. The sample holder of claim 1, wherein the proximal end comprises an open portion for providing a second access to the chamber.

21. The sample holder of claim 20, wherein the proximal end is configured for placement in close proximity to at least one of a flat light permeable material, an optical filter and a lens.

22. The sample holder of claim 21, wherein the placement of the proximal end with respect to at least one of a flat light permeable material, an optical filter and a lens facilitates flow through of the sample.

23. A system comprising the sample holder as claimed in claim 1, the system further comprising at least one optical element configured for at least one of focusing, guiding and filtering light emitted from the distal end of the sample holder.

24. The system of claim 23, wherein data associated with the light from the sample holder can be collected repeatedly.

25. The system of claim 23, comprising a plurality of the sample holders.

26. A system comprising the sample holder as claimed in claim 1, the system further comprising a detector for detecting the light emitted from the distal end of the sample holder.

27. The system as claimed in claim 26, wherein the detector comprises at least one of a spectrometer, photomultiplier tube (PMT), charge coupled device (CCD), CMOS imaging arrays or photodiode, and an optical detector.

28. The sample holder of claim 1, further comprising electrodes configured within the chamber, whereby when a voltage difference is applied between the electrodes, electrochemiluminescence is facilitated for detection.

29. The sample holder of claim 1 wherein the outer longitudinal surface comprises a reflective material.

30. The sample holder of claim 1, further comprising means for controlling the temperature of the sample.

31. The sample holder of claim 1, wherein the proximal end encloses the sample, whereby the sample does not exit the chamber through the proximal end.

* * * * *